United States Patent
Montagu

(10) Patent No.: US 6,638,770 B1
(45) Date of Patent: Oct. 28, 2003

(54) CLEANING DEPOSIT DEVICES THAT GENERATE MICROARRAYS

(75) Inventor: Jean I. Montagu, Brookline, MA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/199,968

(22) Filed: Jul. 20, 2002

Related U.S. Application Data

(63) Continuation of application No. PCT/US01/04285, filed on Feb. 9, 2001, which is a continuation-in-part of application No. 09/501,099, filed on Feb. 9, 2000, now Pat. No. 6,428,752.

(51) Int. Cl.[7] .............................. G01N 1/00; B08B 3/00
(52) U.S. Cl. ...................... 436/174; 118/300; 134/22.1; 134/44; 134/50; 134/85; 422/63; 422/100; 436/180
(58) Field of Search ................ 422/63, 68.1, 99, 422/100, 102, 103, 104, 117; 436/43, 46, 174, 180; 204/450, 451, 600, 601; 118/300; 134/22.1, 22.11, 22.12, 44, 50, 85, 88, 94.1; 15/300.1, 302, 303, 320, 322; 427/421

(56) References Cited

U.S. PATENT DOCUMENTS

| | | | | |
|---|---|---|---|---|
| 2,868,020 | A | 1/1959 | Williams, Jr. | 73/432 |
| 3,329,964 | A | 7/1967 | Mutschler et al. | 346/78 |
| 3,334,354 | A | 8/1967 | Mutschler | 346/140 |
| 3,568,735 | A | 3/1971 | Lancaster | 141/238 |
| 4,041,995 | A | 8/1977 | Columbus | 141/275 |

(List continued on next page.)

FOREIGN PATENT DOCUMENTS

| | | |
|---|---|---|
| EP | 0 373 203 | 6/1990 |
| WO | WO 95/04594 | 2/1995 |
| WO | WO 95/09248 | 4/1995 |
| WO | WO 98/55852 | 12/1998 |
| WO | WO 99/36760 | 7/1999 |

OTHER PUBLICATIONS

International Search Report mailed on Jun. 25, 2001 in PCT Application PCT/US01/04285.
Pease et al.; "Light–generated oligonucleotide arrays for rapid DNA sequence analysis"; *Proc. Natl. Acad. Sci. USA*; vol. 91, pp. 5022–5026, May 1994.
Southern et al.; "Molecular interactions on microarrays"; The Chipping Forecast; *Nature Genetics*; vol. 21, pp. 5–9; Jan. 1999.
Trent et al., "Workshop on Methods and Applications of DNA Microarray Technology"; Jan. 11–13, 1998.
"Microfiltration Apparatus"; *Chromatography Electrophoresis Immunochemistry Molecular Biology HPLC*; catalogue M 1987.
Hames et al.; "Nucleic Acid Hybridization: A Practical Approach"; *IRL Press* Oxford England; 1985.
"BioRobotics Latest Developments"; BioRobotics, Beckman Instruments, Inc.; 1997.
Abstracts of papers presented at the 1994 meeting on Genome Mapping & Sequencing; pp. 48, 60–62, 198, 203, 296–297; May 11–15, 1994.

(List continued on next page.)

Primary Examiner—Joseph Drodge
(74) Attorney, Agent, or Firm—Philip L. McGarrigle; Ivan D. Zitkovsky

(57) ABSTRACT

An apparatus for depositing an array of spots on a receiving surface includes a fluid source, a deposit device that includes a drop-carrying surface, and a cleaning device. The deposit device and a fluid source are cooperatively arranged to deposit a spot(usually created by a drop) on a receiving surface. The cleaning device is constructed and arranged to clean the drop-carrying surface by employing a flow of cleaning fluid or another cleaning matter such as small particles the flow being arranged to prevent contaminating back flow.

56 Claims, 12 Drawing Sheets

U.S. PATENT DOCUMENTS

| | | | |
|---|---|---|---|
| 4,096,825 A | 6/1978 | Golias et al. ................ | 181/221 |
| 4,142,656 A | 3/1979 | Smith et al. ................. | 222/325 |
| 4,322,063 A | 3/1982 | Fishbeck et al. ............ | 267/160 |
| 4,340,390 A | 7/1982 | Collins et al. | |
| 4,387,384 A | 6/1983 | Sue ............................ | 346/140 |
| 4,434,672 A | 3/1984 | Williamson et al. ..... | 73/864.22 |
| 4,441,532 A | 4/1984 | Hrubesh ........................ | 141/1 |
| 4,452,899 A | 6/1984 | Alston ......................... | 436/46 |
| 4,567,585 A | 1/1986 | Gelbart ........................ | 369/97 |
| 4,635,488 A | 1/1987 | Kremer ................... | 73/864.22 |
| 4,656,007 A | 4/1987 | Douchy et al. .............. | 422/64 |
| 4,659,677 A | 4/1987 | Glover et al. ............... | 436/174 |
| 4,737,344 A | 4/1988 | Koizumi et al. ............ | 422/100 |
| 4,981,783 A | 1/1991 | Augenlicht .................... | 435/6 |
| 5,160,378 A | 11/1992 | Tuunanen et al. ......... | 134/25.1 |
| 5,202,231 A | 4/1993 | Drmanac ................... | 422/100 |
| 5,204,268 A | 4/1993 | Matsumoto ................... | 436/44 |
| 5,213,764 A | 5/1993 | Kerr et al. .................. | 422/100 |
| 5,223,225 A | 6/1993 | Gautsch ....................... | 422/100 |
| 5,262,128 A | 11/1993 | Leighton et al. ............ | 422/100 |
| 5,306,510 A | 4/1994 | Meltzer ........................ | 422/65 |
| 5,338,688 A | 8/1994 | Deeg et al. ................. | 436/180 |
| 5,344,666 A | 9/1994 | Levine ....................... | 427/2.11 |
| 5,428,690 A | 6/1995 | Bacus et al. ................ | 382/128 |
| 5,436,129 A | 7/1995 | Stapleton ........................ | 435/6 |
| 5,443,791 A | 8/1995 | Cathcart et al. .............. | 422/65 |
| 5,492,806 A | 2/1996 | Drmanac et al. .............. | 435/5 |
| 5,525,464 A | 6/1996 | Drmanac et al. .............. | 435/6 |
| 5,540,891 A | 7/1996 | Portmann et al. ............ | 422/102 |
| 5,551,487 A | 9/1996 | Gordon et al. ................. | 141/1 |
| 5,607,861 A | 3/1997 | Komatsu et al. ............. | 436/50 |
| 5,626,740 A | 5/1997 | Seto et al. ................... | 205/789 |
| 5,665,312 A | 9/1997 | Sperber et al. | |
| 5,700,637 A | 12/1997 | Southern et al. | |
| 5,756,050 A | 5/1998 | Ershow et al. .............. | 422/100 |
| 5,770,151 A | 6/1998 | Roach et al. ................. | 422/63 |
| 5,800,992 A | 9/1998 | Fodor et al. .................... | 435/6 |
| 5,807,522 A | 9/1998 | Brown et al. ................. | 422/50 |
| 5,882,930 A | 3/1999 | Baier .......................... | 436/49 |
| 5,895,630 A | 4/1999 | Skaborn et al. ............. | 422/100 |
| 6,090,251 A | 7/2000 | Sundberg et al. ........... | 204/600 |
| 6,101,946 A | 8/2000 | Martinsky ................... | 422/100 |
| 6,269,846 B1 * | 8/2001 | Overbeck et al. ........... | 436/180 |
| 6,323,043 B1 * | 11/2001 | Caren et al. ................. | 436/180 |
| 6,428,752 B1 * | 8/2002 | Montagu ..................... | 422/104 |
| 6,551,557 B1 * | 4/2003 | Rose et al. .................. | 422/100 |

OTHER PUBLICATIONS

Gilson; "Raising The Speed Limit on Liquid Handling . . . Again!" advertisement p. 1, Undated.

Castellino, Alexander M.; "When the Chips are Down"; *Genome Research*; vol. 7, No. 10; (1997), pp. 943–946.

Elkins, R.P., et al.; "Multianalyte Immunoassay: The Immunological "Compact Disk" of the Future"; *Journal of Clinical Immunoassay*; vol. 13, No. 4; (1990), pp. 169–181.

Normag, Northern Magnetics Inc, company brochure, undated.

Normag, "Single Axis High Performance Llinear Stepper Motors", product description, p. 1, undated.

"The Perfect Solution for Your Testing Problem", © Ostby Barton, (1997); product description, p. 1.

BioRobotics, "The MicroGrid", product description, p. 2, undated.

"Gridding & Replicating Application", Revised: Nov. 1997 © PBA Technology Ltd., pp. 1–2.

Geysen, H.M., et al.; "Strategies for epitope analysis using peptide synthesis"; *Journal of Immunological Methods*; vol. 102; (1987), pp. 259–274.

Graves, David J., et al.; "System for Preparing Microhybridization Arrays on Glass Slides"; *Analytical Chemistry*; vol. 70, (1998) pp. 5085–5092.

Kalachikov, S., et al.; Colony Section with an Automated 383–Pin High–Density Replicating Tool (HDRT); Biorobotics, © 1996 Beckman Instruments, Inc.; pp. 1–7.

Lemieux, B., et al.; "Overview of DNA chip technology"; *Molecular Breeding*; vol. 4, (1998); pp. 277–289.

* cited by examiner

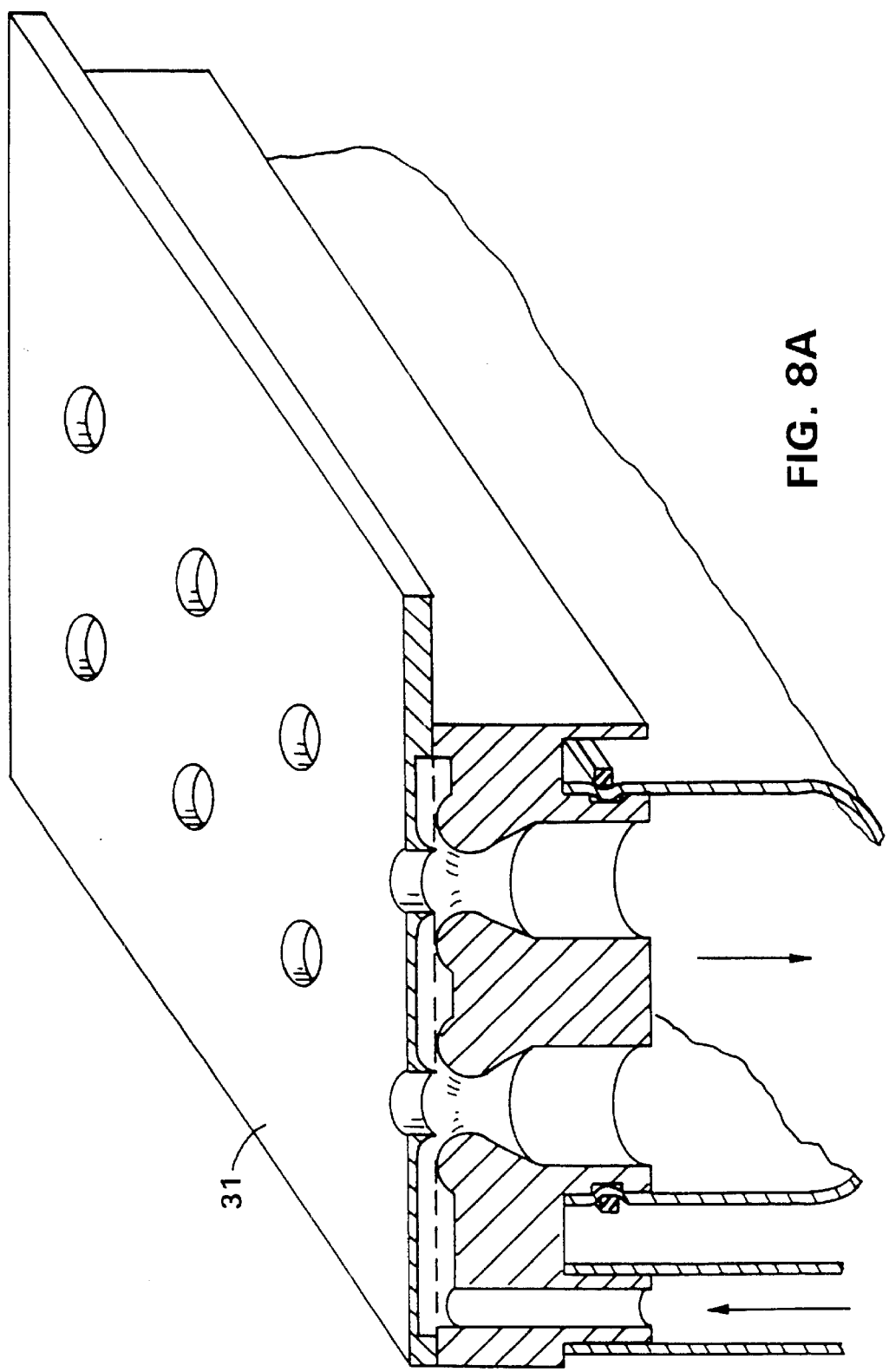

CLEANING DEPOSIT DEVICES THAT GENERATE MICROARRAYS

This application is a Continuation of PCT/US01/04285, filed Feb. 9, 2001, which is a Continuation-In-Part of U.S. patent application Ser. No. 09/501,099, filed Feb. 9, 2000, now U.S. Pat. No. 6,428,752.

BACKGROUND OF THE INVENTION

The invention relates to devices and systems that deposit small quantities of fluid upon substrates in a precise manner and in arrays of desired density and consistency, and especially to cleaning such systems and other equipment in the laboratory. The invention is useful, for instance, in preventing cross-contamination when carrying out reactions, in providing accurate overlays of deposits, and, in particular, in preparing microscope slides and membranes with biological materials, for instance, microarrays for drug delivery, gene research and clinical use.

In well developed biological analytical technology, and in recently developed biochip technology, creation of dense arrays of fluorescently labeled micro-organisms and DNA assays in a two dimensional field is performed. It is desirable to place the arrays on a conventional microscope slide, or other carrier and to create many such slides simultaneously in a manufacturing process.

For biochip technology to proceed to complete fruition, as well as to improve the application of previous analytical techniques, economical instruments and systems have been needed that can, without contamination, rapidly and accurately create the dense array of objects over a large field portion of a glass microscope slide or a slide-like member that occupies an area approximately 22 mm wide and 50 mm long of a slide that is nominally 25 mm×75 mm.

In the deposition upon a microscope slide of discrete, minute quantities of a large variety of fluid materials, the volume deposited at a discrete spot typically may be from a few pico liter to a fraction of a micro liter, depending upon the application. The devices for forming such deposits are small and may have high surface energy. The biological material carried in this fluid can range from a few strands of short oligonucleotides in a water solution to a high concentration of long strands of complex proteins. The properties of these fluids vary enormously. Some are akin to water while others are far more viscous, resembling a light oil or honey. The range of fluids that may be employed also exhibits wide differences in other properties that make clean up difficult.

Such a large range of property variations in fluids of interest has caused difficulties for any single type of process to operate over a wide range to produce the desired array of deposits, to maintain such instrument clean and avoid contamination of the deposited array, the used biological material and various fluids used for deposition.

SUMMARY OF THE INVENTION

One purpose of the invention is to provide a technology deposition of very small drops of fluids, and arrays of drops, e.g. drops that form spots of less than about 375 or 300 μm diameter, and in important cases, very much smaller than that, deposited at correspondingly high densities. As used in this application, the term fluid "drop" refers to a very small quantity of fluid or fluid including solid material, and not to any particular shape of the fluid volume. When depositing an array of drops, it is important to avoid contamination in progressing from work with one material to another as well as contamination of the source material.

The present invention relates to methods and apparatuses used for depositing a biological or other material on a receiving surface and creation of an array. The deposited array is suitable for sample acquisition, preparation microscopic analysis, reaction or other purposes. The deposited array is useful in a variety of biological applications some of which are described in U.S. Pat. Nos. 4,965,188; 5,143,854; 5,384,261; 5,856,174, which are incorporated by reference.

According one aspect, an apparatus for depositing an array of spots on a receiving surface includes a fluid source (or source means), a deposit device that includes a drop-carying surface (or deposit means), and a cleaning device (or cleaning means). The deposit device and a fluid source are cooperatively arranged to deposit a spot (usually created by a drop) on a receiving surface. The cleaning device is constructed and arranged to clean the drop-carying surface by employing a flow of cleaning fluid (or another cleaning matter such as small particles). The apparatus may include additional optional elements discussed below and/or shown in the drawings. The cleaning device may include a fluid jet constructed and arranged to blow the cleaning fluid. The fluid jet may be constructed and arranged to blow,the cleaning fluid at least partially along a length of the deposit device toward the drop-carrying surface. The drop-carrying surface may be located at least partially within a confinement chamber.

The deposit device may have a pin-like structure with the drop-carrying surface disposed in a distal end of the pin-like structure. The drop-carrying surface may have a diameter less than 375 micron, preferably less than 300 micron, preferably between about 15 and 250 micron. The pin-like structure may include sides that intersect with an end surface that defines a rim of the drop-carrying surface.

The apparatus may include one or several fluid sources. The fluid source may include or be used with a mobile supply device, associated with the deposit device, and arranged to supply material for deposition of the array of spots. The fluid source may include or be used with a mobile local supply device arranged to move partially with the pin-like structure. The deposit device and the mobile supply device may be movable together to the cleaning device in response to a control system.

The mobile local supply device may include an annular member through which the deposit device operates by a relative motion of the drop-carrying surface, and the cleaning device may include a nozzle for directing a flow of the cleaning fluid past the annular member and the drop-carrying surface.

The apparatus may include one or several cleaning devices. The cleaning device is constructed and arranged to deliver the cleaning fluid at least partially to the mobile supply device or the mobile local supply device. The mobile local supply device includes a ring-like structure located near the drop-carrying surface. The cleaning device may be constructed and arranged to deliver the cleaning fluid at least partially to the ring-like structure and the drop-carrying surface.

The apparatus may further include a drying device constructed to discharge drying fluid. Alternatively, the drying device is included in the cleaning device and is constructed to discharge drying fluid using the fluid jet used for cleaning. The fluid jet may have various designs and may include a circular nozzle constructed to emit a conical flow of the cleaning or drying fluid achieving venturi effect, or may include an annular or other nozzle.

The apparatus may further include a reservoir for receiving the cleaning or drying fluid. A vacuum pump or another pumping device may be associated with the reservoir. The reservoir receives the cleaning or drying fluid emitted from the fluid jet. The fluid jet or nozzle may be located inside a containment chamber or outside the chamber. The pump may create a pressure differential for removing the cleaning or drying fluid emitted from the fluid jet.

The apparatus may include two or more fluid paths associated with at least two fluid reservoirs and connectable to the fluid jet. The apparatus may be associated with a control system arranged to control a flow velocity of the cleaning fluid. The apparatus may be associated with a control system arranged to select a type of the cleaning fluid. The control system may be arranged to select the type of the cleaning fluid at a source location. The cleaning fluid is selected from one of the following compressed gas, high-pressure liquid, aerosol and heated gas.

The apparatus may include four or more deposit devices and a mechanism for moving each deposit device independently toward and away from the receiving surface to deposit respective drops at respective deposit locations on the receiving surface. Alternatively, the mechanism may move the deposit devices simultaneously, relatively, toward and away from the receiving surface to deposit respective drops at respective deposit locations on the receiving surface. The deposit devices may be mounted on a common support that is driven by a common driver to deposit respective fluid drops on the receiving surface. These deposit devices may be associated with respective storage rings, wherein the storage rings are mounted on a common storage support driven by a common storage drive.

The apparatus may include a mobile fluid storage device that is movable relative to an array of deposit locations, wherein the mobile supply device is constructed and arranged to resupply the deposit device at various locations along the array. Preferably the deposit device and the mobile storage device are constructed to supply drops to the deposit device in the immediate vicinity of the deposit locations for respective drops and preferably being coupled for transverse motion relative to the array and decoupled for movement of the deposit device toward and away from the receiving surface.

According to yet another aspect, an apparatus for depositing fluid dots on a receiving surface in an array (e.g., for microscopic analysis reaction and the like) includes a deposit device and a fluid source which are cooperatively related to enable the deposit device to precisely size a drop of fluid of small diameter on a drop-carrying surface of the device, transport mechanism for positioning the device at a precisely referenced lateral position over the receiving surface and drive mechanism for moving the deposit device, relatively, in deposition motion toward and away from the surface, the apparatus adapted, by repeated action, to deposit the drops of fluid precisely in a desired array, and then to proceed to a cleaning station where the instrument is cleaned and then to a resupply station for further action with regard to other materials, free of contamination, preferably the apparatus being computer controlled.

Preferred embodiments have one or more of the following features.

A cleaning station comprises a fluid jet arranged to blow down along the length of the deposit device toward its drop-depositing end, the jet and device being within a confinement chamber thus preventing contamination.

The deposit device is a pin or pin-like structure having an end surface that carries the fluid drop, preferably the pin or pin-like structure having sides that intersect with the end surface to define a sharp peripheral drop-defining rim.

According to yet another aspect, an apparatus for depositing fluid drops on a receiving surface includes a deposit device and a fluid source which are cooperatively related to provide to a drop-carrying surface of the deposit device a precisely sized drop of fluid, and a cleaning system that effectively cleans the pin, the deposit device being a pin or pin-like structure having an end surface that serves as the drop-carrying surface, the pin or pin-like structure having sides that intersect with the end surface to define a sharp peripheral drop-defining rim.

Preferred pins or pin-like structures have an end surface that is generally flat and side surfaces that are cylindrical and smooth.

In many important cases, the fluid source is a mobile fluid storage device that is movable relative to an array of deposit locations, the fluid storage device being constructed and arranged to resupply the deposit device at various locations along the array.

According to yet another aspect, an apparatus for depositing fluid drops on a receiving surface, includes a deposit device and a fluid source which are cooperatively related to provide to the deposit device a drop of fluid, transport mechanism for positioning the deposit device over a receiving surface and drive mechanism for moving the deposit device, relatively, in deposition motion toward and away from the receiving surface, the apparatus adapted, by repeated action, to deposit the drops of fluid in a desired array, the fluid source being a mobile fluid storage device that is movable relative to the array of deposit locations, the fluid storage device being constructed and arranged to resupply the deposit device at various locations along the array, the system adapted to effectively clean the instruments between changes of fluids.

In preferred embodiments employing a mobile storage device, the deposit device and the mobile storage device are constructed to supply drops to the deposit device in the immediate vicinity of the deposit locations for respective drops, preferably the mobile fluid storage device and the deposit device being coupled for transverse motion relative to the array and decoupled for movement of the deposit device toward and away from the receiving surface.

In many cases the mobile storage devices or mobile local storage devices are constructed and arranged to be replenished from a remotely located large reservoir. In many cases a mobile storage device holds a volume of fluid having a free surface into which the deposit device is lowered and raised to obtain a fluid drop, preferably the mobile storage device being constructed to store a multiplicity of isolated fluid volumes in the wells of a multiwell plate, the apparatus constructed to obtain its fluid from a selected volume of the plate.

In other important cases a mobile local storage device defines a generally annular fluid retention surface or ring (the term "annular" or "ring" being used to refer broadly to a member that has opposed, or adjacent, surfaces that can hold a mass of fluid between them by surface tension effects, accessible to a deposit device) and the deposit device is constructed to move within the annular retention surface from retracted to extended positions, in the retracted position the drop-carrying surface of the deposit device being retracted from the surface of fluid retained by the annular surface of the storage device, and in the extended position the drop-carrying surface of the deposit device being projected through and beyond the surface of the retained fluid. Advantageously, the cleaning device can cleans the pin and ring simultaneously.

According to yet another aspect, an apparatus for depositing fluid drops on a receiving surface in an array suitable for microscopic analysis, comprising a deposit device and a fluid source which are cooperatively related to provide to a drop-carrying surface of the deposit device a precisely sized drop, and a drive mechanism for moving the deposit device, relatively, in deposition motion toward and away from the receiving surface, the storage device defining a generally annular fluid retention surface, and the deposit device being constructed to move within the annular retention surface from retracted to extended positions, in the retracted position the drop-carrying surface of the deposit device being retracted from the surface of the fluid retained by the annular surface of the storage device, and in the extended position the drop-carrying surface of the deposit device being projected through and beyond the surface of the retained fluid, the relative position of the deposit device and the storage surface being adjustable so that at the cleaning station an optimal relationship for cleaning can be achieved.

In preferred embodiments, a member that defines an annular fluid retention surface is associated with a driver that moves the member relative to the deposit device to a replenishment volume in which the member is immersed to receive a supply of fluid, and to a cleaning position when the system arrives at the cleaning station.

In certain preferred embodiments the deposit device is a pin or pin-like structure e.g. having one or more of the features described above, the pin or pin-like structure being mounted within the confines of an annular fluid retention surface and arranged to move axially relative thereto.

The apparatus of any of the aspects and preferred embodiments described preferably include a control system adapted to control relative movement of the deposit device to a depositing relationship to the receiving surface and a cleaning relationship to the cleaning system.

According to yet another aspect, an apparatus for depositing an array of dots on a receiving surface, comprising a deposit device in the form of a pin or pin-like structure having an end surface capable of precisely defining a small drop of fluid, a source of fluid for the deposit device, mechanism for moving the deposit device relatively over an array of spaced apart deposit locations of a receiving surface, mechanism for repeatedly moving the deposit device, relatively toward and away from the receiving surface to deposit respective drops of fluid at selected deposit locations, a cleaning system, and a control system adapted to control relative movement of the deposit device between a resupply relationship to the source, a depositing relationship to the substrate and a cleaning relationship to the cleaning system.

In embodiments in which the deposit device is associated with a mobile supply device that travels with it, the deposit device and mobile supply device are preferably movable together to the cleaning system in response to the control system, preferably the mobile supply device being an annular member through which the deposit device operates. Preferably the cleaning system has a nozzle for directing a flow of air past the annular structure, preferably a cleaning or drying station comprising a circular nozzle is constructed to discharge a conical flow of fluid, preferably compressed air, high pressure liquid, an aerosol or heated air against a deposit device or mobile fluid source, preferably the deposit device being a pin or pin-like structure surrounded by a mobile reservoir in the form of an annular member capable of holding a supply of fluid by surface tension effects, the nozzle flows directed to dislodge retained fluid, to clean or to dry the respective parts; in some cases, preferably a circular storage device is associated with a heater, e.g., an induction heater.

Preferably, each device to be cleaned has its own cleaning chamber to which it travels, for removal of previous fluid, washing and drying in a so-called "one stop shop" designed to prevent contamination during cleaning.

In certain preferred embodiments of the various aspects and features described there are provided a set of at least two of the deposit devices, preferably many more, at least one fluid source for providing a drop of fluid on each deposit device, and mechanism for moving the pins together transversely over an array of spaced apart deposit locations of the receiving surface, and to a cleaning station for the respective deposit devices, preferably there being at least four of the deposit devices comprising a deposit head. Preferably the apparatus includes mechanism for repeatedly moving each deposit device independently, or mechanism for moving each deposit device simultaneously, relatively, toward and away from the supply device for resupply, the receiving surface to deposit respective drops at respective deposit locations on the receiving surface, and, optimally the cleaning station.

For simultaneous actuation, preferably two or more deposit devices are mounted on a common support, driven by a common driver to deposit respective fluid drops on the receiving surface. In cases in which each deposit device is associated with a respective storage ring, the storage rings are also mounted on a common support, driven by a common drive; preferably the spacing of the rings corresponds to the spacing of a multiwell storage plate into which the rings are immersed for resupply. In cases in which the deposit device is lowered directly into fluid and raised to obtain its drop, preferably the spacing of the deposit devices corresponds to the spacing of wells of a predetermined multiwell plate, the multiwell plate being a mobile fluid supply that is constructed to accompany the deposit device across the substrate. In the case of supply rings or direct dipping of the deposit devices, preferably the spacing corresponds to well-to-well spacing of wells of a 96, 192, 384, 864 or 1536 well plate, or a spacing of 9 mm or a submultiple of 9 mm. Likewise in this case and others, the deposit devices register with discrete cleaning stations for the individual elements, in which preferably, high speed fluid flow is directed toward the instruments being cleaned, but in a direction away from the work environment. Preferably, the high speed flow induces air flow from the work environment along the device being cleaned to create a negative pressure condition in the work environment and avoid backflow of contaminants from the containment chamber.

The apparatus of any of the foregoing is preferably constructed to mount a number of microscope slides or slide-like structures to serve as the receiving surface, and a control system is constructed and arranged to deposit drops of fluid in selected locations on the slides or slide-like structures, preferably the fluid source comprising a source of biological fluid.

Preferably, for depositing fluid drops in a dense array of mutually isolated dots, a deposit assembly is constructed to travel to a cleaning station, and comprises a fluid source for repeatedly providing a discrete drop of fluid on the tip of the deposit device, mechanism for moving the device relatively over an array of spaced apart deposit locations of a receiving surface, mechanism for repeatedly moving the device, relatively, toward and away from the receiving surfaces to deposit respective dots at respective deposit locations on the surface, preferably the fluid source being a mobile fluid storage device separate from the deposit device, which is generally movable over the array of deposit locations, the fluid storage device being constructed and arranged to resupply the deposit device at various locations with respect to the array.

In certain preferred embodiments of this aspect also, the deposit device is a slidable pin or pin-like structure constructed and arranged to dip into a volume of fluid carried by a mobile storage device, preferably the storage device being constructed to store a multiplicity of isolated fluid volumes, the apparatus constructed to move the supply device relative to the deposit device to select the fluid to be deposited, preferably the storage device being a 96 well plate or a plate having a multiple of 96 wells, and also preferably including at least one driven stage for moving a selected well of a mobile multiwell plate into registry with the deposit device under computer control for enabling motion of the deposit device to dip into and out of the preselected well to provide a drop of the selected fluid to the device.

According to yet another aspect, a deposit apparatus includes a multiplicity of deposit devices as described, mounted for motion together in response to a common actuator, preferably the deposit devices comprising deposit pins or pin-like structures adapted to enter respective cells of a cleaning station of the kind described above.

According to yet another aspect, an apparatus includes a mobile fluid storage device separate from a deposit device and generally movable over an array of deposit locations, the fluid storage device being constructed and arranged to resupply the deposit device at various locations with respect to the array, in one case, preferably the mobile fluid storage device being constructed to store a multiplicity of isolated fluid volumes, the apparatus constructed to move the mobile storage device relative to the deposit device to select the fluid to be deposited, preferably the deposit device being a pin or pin-like structure constructed and arranged, under computer control, to dip into a cleaning station periodically and in operation, dip into a selected volume of fluid carried by the mobile fluid storage device, preferably the mobile fluid storage device being a multiwell plate having 96 wells or multiples of 96 wells, or a spacing of 9 mm or a submultiple of 9 mm and preferably the apparatus including a driven stage for moving the fluid storage device into registry with the deposit device under computer control for enabling dipping of the deposit device into a preselected fluid volume; in another case preferably the mobile storage device is an annular ring that retains a supply of fluid by surface tension.

The present invention also features the method of use of all the described apparatuses. In the various methods, preferably the receiving surface is fragile, or soft, preferably the receiving surface is porous or microporous or fibrous, preferably comprising nitrocellulose, nylon cellulose acetate or poly nylidine fluoride or a gel, preferably the member defining the soft or fragile receiving surface being mounted on a rigid carrier member, either directly or upon an intermediate soft or resilient buffer member.

Preferably the method is employed to deposit a fluid selected from the group of biological fluids described in the specification, preferably the material being a biological probe or a chemical for reaction with biological material, a fluorescing material, an ink, dye, stain or marker, a photoactive material, or a varnish or an encapsulant or an etchant, or a cleaning or neutralizing agent.

According to yet another-aspect, the method of depositing a biological fluid with a pin (or a pin-like structure) comprising supporting fluid within a ring (or a ring-like structure) by surface tension, and moving the pin (or pin-like structure) through the ring (or the ring-like structure) in the manner that a relatively small drop of the fluid is held at the end of the pin (or the pin-like structure) by surface tension and deposited on a receiving surface, and moving the structures to a cleaning station.

BRIEF DESCRIPTION OF THE DRAWINGS

In the Figures:

FIG. 1A depicts a mobile sub-reservoir that travels from one deposit position to another with a separate deposit device illustrated as a deposit pin.

FIG. 8 is a perspective, partially cut-away view of a preferred cleaning module while FIG. 8A is a magnified view of a portion of FIG. 8.

FIG. 9 is a view of a preferred relationship of a pin and associated mobile reservoir ring while

A. PREFERRED EMBODIMENTS

Figure 1:
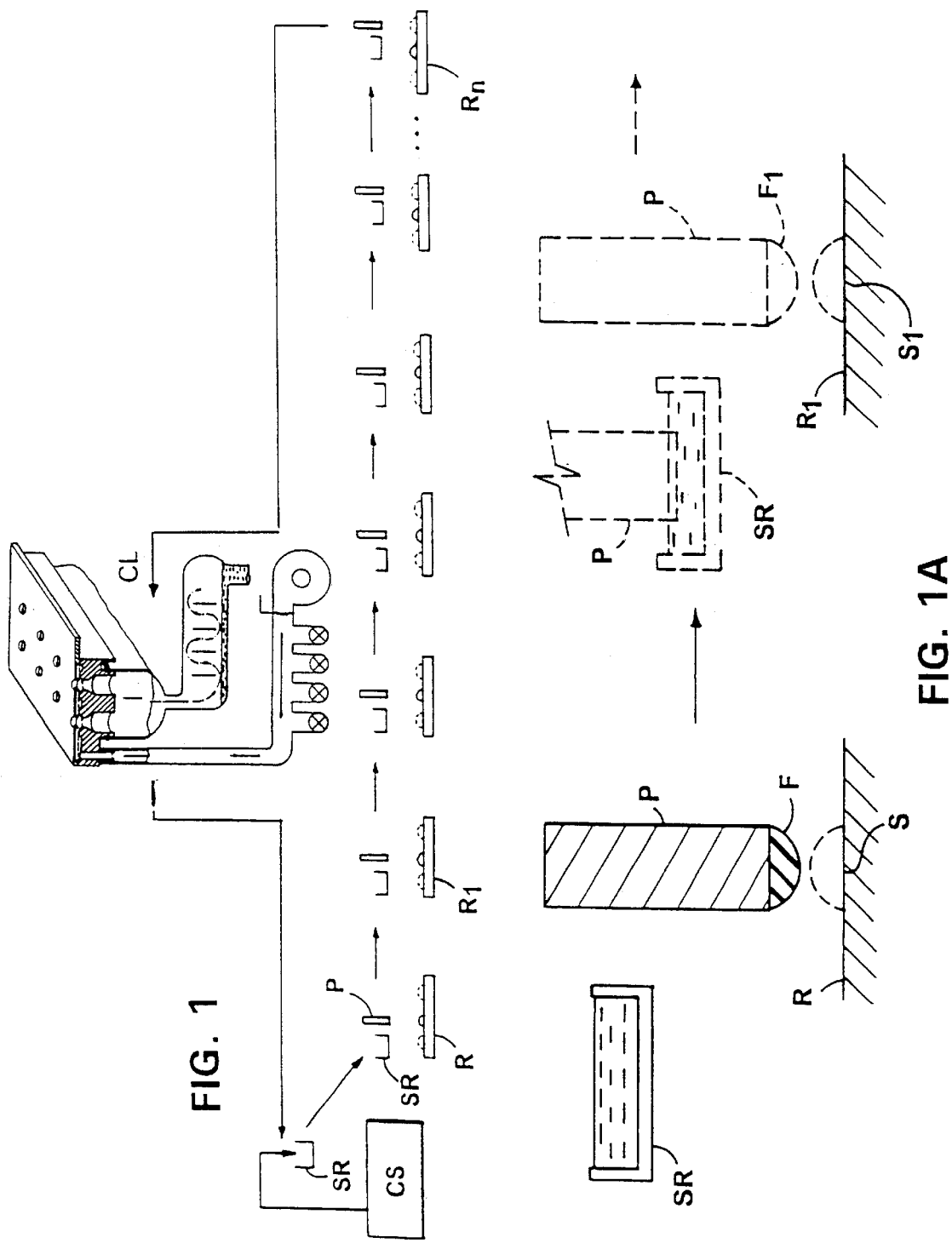
FIG. 1 depicts a spotting system employing the deposit action depicted in FIG. 1A, combined with a cleaning station and a central supply of fluid specimen.

In preferred embodiments a deposit pin D of small cross-section is employed with a mobile fluid reservoir to which the pin is repeatedly exposed, the pin being sized and shaped to define and retain on its tip a drop of fluid from the reservoir, the drop containing only enough material to deposit a single dot. The fluids and the resultant dots permissibly exhibit a wide range of properties such as viscosity, evaporative characteristics, surface tension, wetability, surfactant characteristic, dynamic contact angle and free surface energy.

Presently we prefer that the rim of the tip of the pin be "square", i.e. that, in profile, the end surface of the tip of the pin be substantially at a right angle to the side surface of the pin, and that the pin side surfaces be smooth. Preferably the pin is round in transverse cross-section, though it may be of other shapes.

It is found that arrays of fluid dots between about 20 microns to 375 microns can be deposited using biologic fluids of conventional concentrations, by employing deposit pins that have, in their tip regions, a wire or wire-like geometry of diameter (true diameter or cross-section dimension) between about 0.001 inch (25 microns) and 0.015 inch (375 microns). The smaller tips, i.e. tips smaller than 0.012 inch (300 microns) are referred to here as "microtips". A preferred range of tip sizes is between 50 microns and 250 microns.

Tightly packed arrays of deposited dots of fluid can be achieved, i.e. arrays with center-to-center spacing between dots of less than three times the dot diameter, often only twice or one and one half times the dot diameter.

Provision of a suitable mounting and drive of the deposit pin enables a low and predictable contact force upon the receiving substrate (a "soft landing") despite variations in the height of the substrate, e.g. due to variations in thickness of microscope slides or slide-like members upon which the fluid dots are applied. Superior results can be obtained by controlling the deposit pin force upon the substrate to less than the order of one gram, or 0.5 gram, preferably about 0.3 gram.

The systems enable spotting of, e.g., a full set of 40 microscope slides with 10,000 spots per slide, a process that may require a few hours to a few weeks, depending upon the number of pins operating simultaneously in one head. The instrument may operate unattended for many hours at a time.

In preferred mechanical systems, the pin is compliantly mounted and responds to resistance force transmitted to the pin by the fluid or mechanical contact with the substrate, so that the tip of the pin stops despite overtravel of the driver. Different deposition systems are described in the PCT application PCT/US99/00730 (WO 99/36760), entitled "Depositing Fluid Specimens On Substrates, Resulting Ordered Arrays, Techniques For Analysis Of Deposited Arrays", which is incorporated by reference.

B. MOBILE FLUID RESERVOIRS AND INTERACTION WITH DEPOSIT PINS AND CLEANING STATION

For making a succession of deposits of the same fluid, as when preparing a number of microscope slides or membranes or providing redundant deposits on a single substrate, a mobile sub-reservoir, periodically re-supplied from a stationary central supply, travels with a deposit device to be near the deposit locations.

As illustrated in FIG. 1A, a deposit head comprises the deposit pin P and the sub-reservoir SR which is sized to contain sufficient sample to enable deposit of a number of dots before being resupplied.

After deposit of drop F at target S, e.g. on a microscope plate R or a plate carrying a delicate or soft membrane, the assembly proceeds to plate $R_1$, pin P is resupplied with drop $F_1$ by being dipped into and raised from the accompanying sub-reservoir SR, the new drop is then deposited at target point $S_1$ at plate $R_1$, and so on.

The system is especially useful for preparing a number of microscope slides or membranes. The central fluid supply CS advantageously is a multiple well plate as conventionally used in microbiology, such as a 96 well plate. Cleaning and drying station CL is also provided. The deposit sequence includes moving the assembly of deposit device and mobile sub-reservoir under computer control through cleaning and drying station CL, thence to central supply CS at which the sub reservoir SR is supplied with a selected fluid sample, e.g. from a selected well of a 96 well plate. Then the group moves over a series of receiving surfaces $R-R_n$, for deposit of fluid dots at selected locations on each, also under computer control. This sequence is repeated a number of times, with controlled selection of different fluid samples (from, e.g., different wells of the central supply CS) for respectively different locations on the plates R or other receiving surfaces. Data that correlates locations with respective specimens is recorded in memory and used in subsequent scanning or reading.

The technique of using a deposit tool that accurately sizes each individual drop, such as the deposit pin with square rim profile at its microtip, combined with a mobile local sub-reservoir that accompanies the tool and carries a volume sufficient to supply a sequence of deposits, has a number of important advantages. The technique, based on small motions, saves time in avoiding repeated travel to a central supply; it avoids evaporation losses of long travel, so that the drop created can be very small and the deposited array very dense; and the dots can be kept consistent in size and concentration or biological content across the array of dots being deposited. The time overhead involved in cleaning, transporting and picking up the specimen is kept small so that, overall, deposits can be made very fast, inexpensively and have desired small size.

In this way a large number (for instance ten to one hundred) identical microscope slides or membranes can readily be prepared by repeated motions over an array of the slides or membranes. Each substrate can carry dots of many different fluids based upon resupply of the sub-reservoir from different wells of a number of multiple well plates introduced to the system, and cleaning between changes of fluid.

Figure 2A:
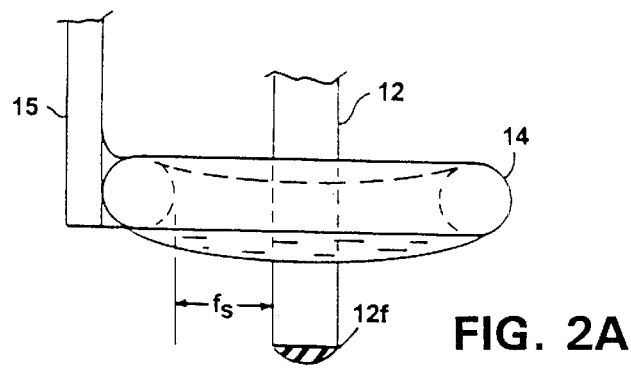
FIG. 2A is a side view and FIG. 2B a top view of a deposit head, comprising a deposit pin and an annular sub-reservoir through which the deposit pin operates.
Figure 2B:
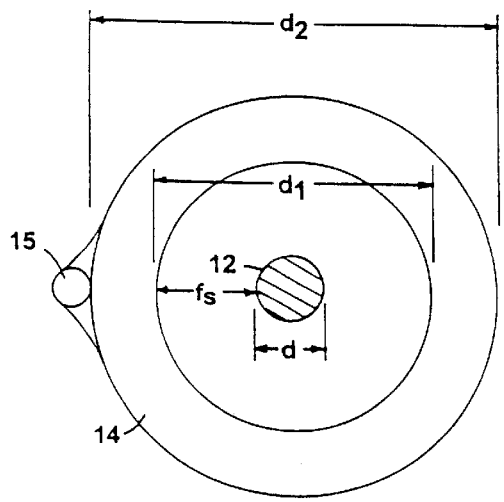
Figure 3A:
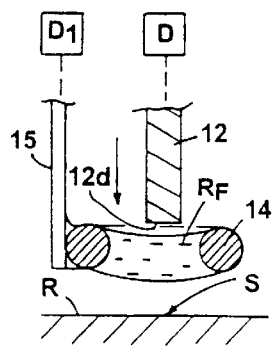
FIGS. 3A–3D depict a sequence of stages of the deposit action of the head of FIG. 2A.
Figure 3B:
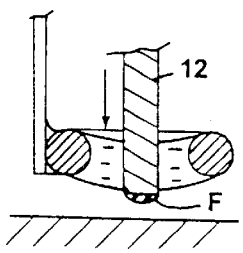
Figure 3C:
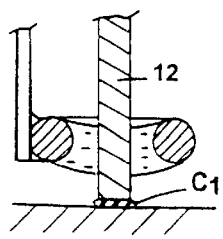
Figure 3D:
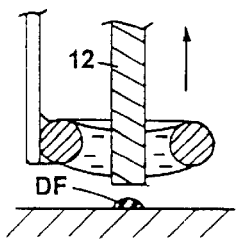

The sub-reservoir and the deposition device are decoupled, in being movable relatively to one another for resupply and for deposit, as well as being coupled or at least coordinated, to move laterally over the receiving surface to produce the series of deposits. The sub-reservoir can move into a resupply position, e.g. by immersion into a well, or under a suitable pipette. It can be made to hold sufficient fluid in excess of that required the internal surfaces of ring 14. This is shown in FIG. 3A. (The pin, for illustration, is shown withdrawn fully above the retained fluid $R_f$, though that is not necessary.) Comparing FIG. 3A with FIG. 2A, by downward movement of the pin tip from above the lower surface of the retained fluid $R_f$ (FIG. 3A), to below that surface (FIG. 3), the tip of the pin, with its sharply defined rim, picks up from the retained fluid $R_F$ a precisely sized volume of fluid as drop F. The drop is then deposited in the sequence shown in FIGS. 3C and 3D. Interestingly, as the pin penetrates the meniscus, surface tension pulls the fluid laterally from the pin with the result that a much smaller amount of fluid can remain on the end of the pin than in the case in which a pin is dipped and then raised from an open supply. In many cases this volume-limiting action is highly desirable, as it permits monolayers or at least very thin spots to be deposited, saving material and providing a uniform fluorescing mass that enables move accurate reading to occur.

Figure 2:
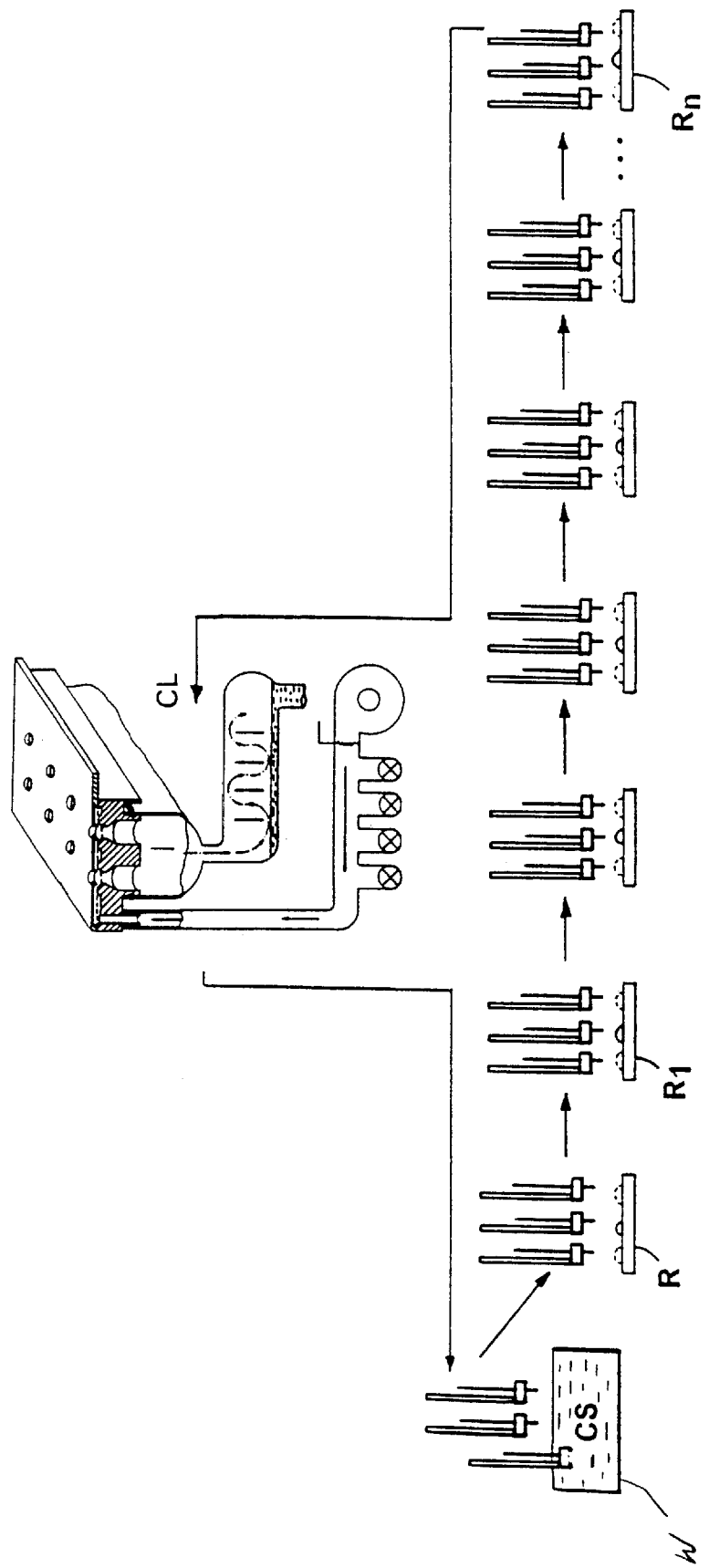
FIG. 2 depicts a spotting system employing the deposit action depicted in FIGS. 2 and 3, combined with a cleaning station and a central supply or fluid specimen.

At the resupply position, see FIG. 2, the annular ring 14 is moved downwardly by its support rod 15 for immersion in the well of the supply plate while the pin 12 remains stationary at a higher elevation, or it may assist in the resupply action, by being present within this ring with its end, for instance, flush with the bottom of the ring, as shown in FIG. 2.

At cleaning and drying stations the lower surfaces of the pin 12 and ring 14' are vertically at the same level.

At a washing station the ring and pin may both be subjected to reciprocation in the same or opposite vertical directions to assist the cleaning process.

Figure 7:
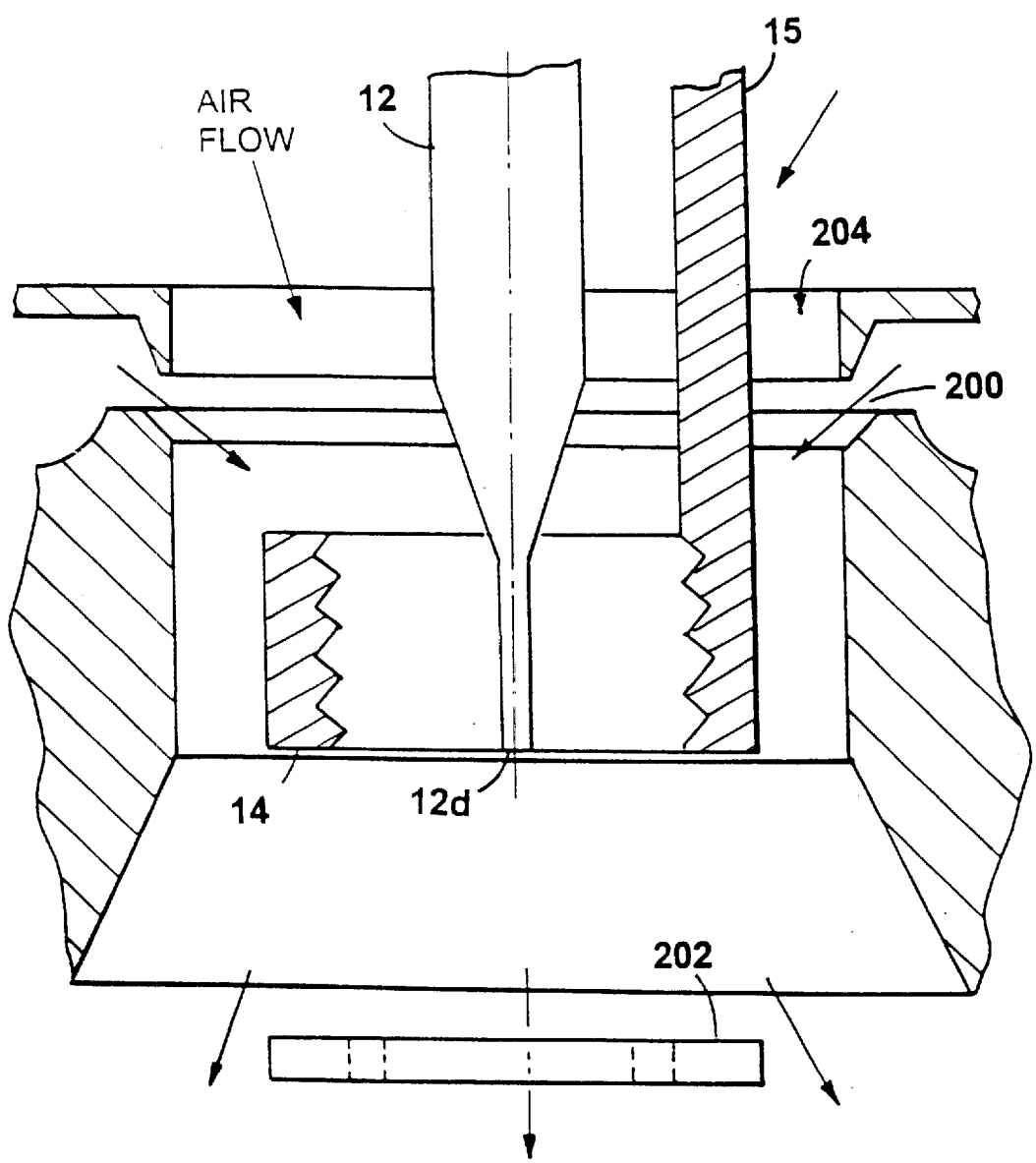
FIG. 7 depicts a station for removing liquid, washing and drying the pin and ring at one-location.

The multipurpose cleaning station illustrated in FIG. 7 is sized to receive deposit pin 12 and supply ring 14. It has an annular nozzle 200 directed inwardly against the pin and ring to subject the parts to a conical flow from fluid sources such as compressed air, pressurized liquid and aerosols. The flow is directed past the parts 12, 14 to a trap having disposable filter 202 that intercepts material being removed from the parts. The trap may be associated with a vacuum pump. As shown, nozzle 200 is associated with a secondary air path 204 to enable nozzle flow to induce a flow of secondary air when desired.

The system of FIG. 7 is useful to remove sample liquid from the parts, to effect cleaning, and to dry the parts. For example the pin and ring are first exposed to one or more simultaneous or successive fluid currents or blasts of continuous or pulsed flow that blow remaining sample fluid from the parts and into the trap. Subsequently, a fluid stream of liquid or air may expose the parts to cleaning fluids such as liquid streams or aerosols containing water-borne detergent. This is followed by rinsing with pure water from the nozzle. Following washing, an air current from the nozzle, supplemented by induced air flow 204, can dry both pin and ring, in which case the air streams may be heated.

There is an advantageous relationship of pin and ring for resupply of the ring. When the ring is immersed in selected well W of a multiwell plate, FIG. 2, the pin is present within the confines of the ring, to help the ring pick up the fluid. The surface tension properties effectively cooperate to compete with the surface tension effects of the walls of the well that resist removal of small quantities of the fluid. In the presently preferred relationship, the bottom tip surface of the pin is substantially aligned with the lower surface of the ring. Withdrawal of the assembly from immersion in well W withdraws a desired amount of fluid, pendent as a large meniscal drop, bounded by the pick up ring. This quantity, protected and supported by the ring, is then available for deposit in tiny drops by repeated projection of the pin through the ring.

The sub-reservoir ring may have various advantageous forms such as axially adjacent circular rings, multi-turn helical shapes, closed cylinders, open rectangular rings, open "U" shaped structures, etc. Thus the term "ring" or "annular ring" as used generally refers to any closed or partially closed structure that, through surface tension effects between adjacent or opposed surfaces, supports a volume of liquid in a space through which a deposit device such as deposit pin 12 can operate. The size of the opening or bore of the ring, as well as the size, for instance, of wire or ribbon that forms the cross-sectional shape of the ring is selected in relation to the properties of the fluid (e.g. viscosity and surface tension), the number of deposits to be made from a given fluid charge in the reservoir ring, and the size of the deposit pin that is to move through the ring.

The size and shape of the deposit pins that cooperate with these and other sub-reservoirs also vary depending upon the application. It is possible to employ pins of various transverse cross-section, e.g. square or hexagonal or even rectangular or oval cross-section of equivalent area to round cross-section pins. Especially for small dots, the pins may advantageously have stepped transverse cross-sections, e.g. may have an extremely small cross-section at the deposit end, to size the deposited drop, stepped to a larger cross-section in the main body, for providing structural stability.

For implementing the broad concept of a local, mobile supply, other techniques than those shown can be employed. An example is a large dip rod, an enlarged version of a deposit pin, from which a large drop depends, which travels with the pin and is visited by the pin by a suitable motion, such as rotation. Such respective dip rods and other devices may be provided cleaning stations similar to that shown.

C. OPERATING SYSTEMS

Some advantageous, novel operating systems that implement the foregoing principles will now be described.

DIP & DOT SYSTEM

The mobile reservoir shown in FIG. 1 can be a multi-well plate. Under computer control, an appropriate X,Y stage brings the chosen fluid resupply well in alignment under the pin. The pin is then controlled: to descend, make contact with (dip into) the reservoir fluid and rise, taking a small amount of fluid in the form of a pendant drop.

The pin is raised sufficiently to permit the pin and reservoir to separate e.g. by computer controlled sideways movement of the reservoir, freeing the pin to descend unobstructed to deposit its small fluid drop on the targeted location on the substrate.

With appropriate transport motions of pin and multi-well supply, the process is repeatable at each location where a sample of the selected fluid is desired, the fluid in the proper well being repeatedly brought into alignment with the proper pin for resupply and deposit in the desired location by computer control. Each time a pin is commanded to receive a fluid from a well different from that of its previous command, the pin is moved by computer control to liquid removal, cleaning and drying station CL, to prevent contamination of the source or the target.

For efficient operation, a multiplicity of pins may be used at spacings that match the pattern of wells, enabling each pin to reach inside a separate well of the multiple well reservoir such as a 96 well plate or a 384 well plate, as are known in the field of biochemistry and analytics.

The pin assembly and its driving mechanisms are preferably mounted on a precision XY gantry as they require good positional accuracy. The multiple well plate may be provided with two degrees of freedom in a plane parallel to the deposition plane and can be indexed under the pin assembly on a separate structure. Because of the relatively large size of the wells, the translation assembly for the plate may have lower positional accuracy than that of the pin. In some cases the multi-pin assembly and the mobile multiwell reservoir share the same X,Y gantry to advantage.

Under computer control, the multiwell reservoir separates in the Y direction from the pin assembly and the Z stage is actuated to cause the pins to form deposits upon substrate R. Then, the multiwell reservoir moves under the raised pins into appropriate alignment, employing both $Y_2$ and $X_2$ motions under computer control. By Z motion the pins $P_A$ dip into the commanded wells for resupply. The pins rise again, the multiwell reservoir moves laterally with $Y_2$ motion out of the way and the deposit process is repeated at new targeted X,Y location of the pins on substrate R or $R_1$. While this mobile reservoir technique is useful with pins of any construction, the advantage of high accuracy of the linear motor indexing system is enjoyed when the pins are constrained in space to a highly accurate repeatable position relative to their carrier, with the high density pin arrangements made possible by the structures shown. Advantage is also taken of the positional accuracy in respect of cleaning. The pins are moved to station CL, FIG. 1, and enter respective holes using the ganged actuator or individual actuators that drive the pins in supply and deposit action.

MULTIPLE PIN PATTERNS

Figure 4A:
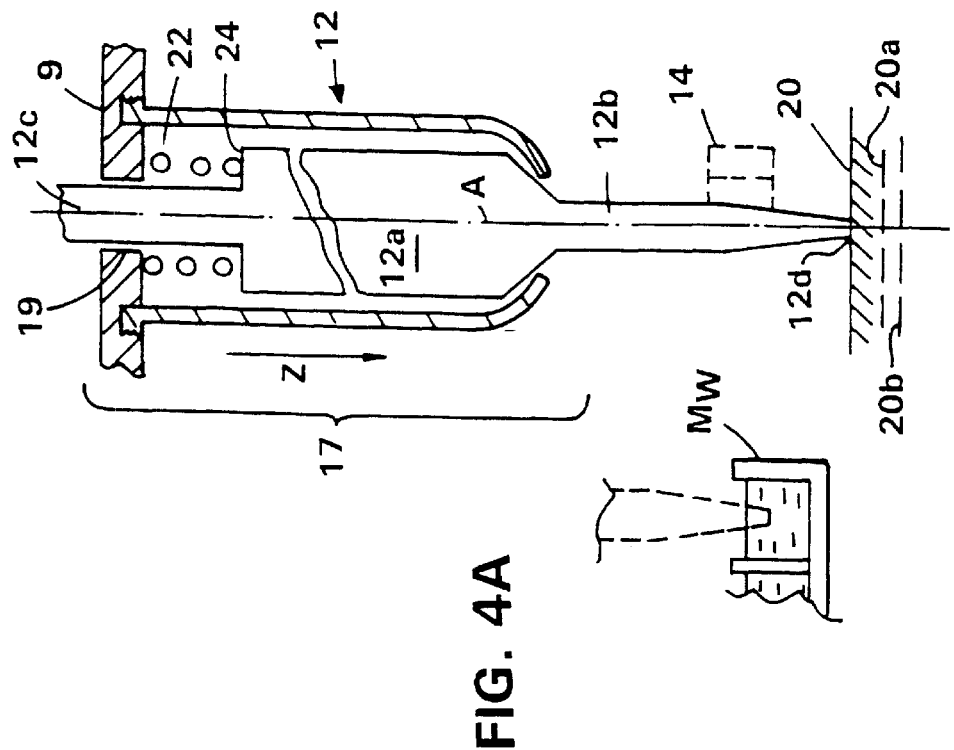
FIG. 4A is a diagrammatic side view of a combination of a deposit pin and a cooperating support that provides lateral constraint of the pin.

In the preferred embodiments, two rows of 4 or more pins P, preferably constructed according to FIG. 4A are spaced apart in a 9 mm square grid pattern matching the spacing of the wells of a 96 well plate. This permits transport of fluid from all 96 wells, 8 wells at a time to an assembled array of microscope slides, and directs the composition of 8 spaced apart blocks of approximate dimension each 8×8 mm on each slide, covering in total approximately 18×54 mm sq. Each pin deposits in a respective one of the 8 blocks simultaneously with a single actuation of the Z drive. The head repeats the action on each of the set of slides with the same fluid, and is then cleaned to be ready for fluid from different wells. The same pin may be used to deposit the same fluid at a number of directed positions in a given block, and/or upon the corresponding block of a number of slides each having the set of 8 spaced apart blocks, the deposits on the slides being much closer than the spacing between wells. By following an appropriate sequence, all wells may be visited by respective pins. Actually the dot size in practice is much smaller than illustrated and dot density much greater, e.g., with as many as 50,000 or 100,000 dots carried by a single microscope slide.)

In a similar preferred embodiment, a grid of 12 pins has 2 rows of 6 pins each, again spaced apart in a 9 mm square grid pattern to match the spacing of the wells of a 96 well plate. This arrangement permits the transport of fluid from all 96 wells, 12 wells at a time, and directs the composition of 12 spaced apart blocks of approximate total area 18×54 mm sq. Similarly, 48 wells can be addressed simultaneously when working with a 384 well plate, having wells spaced 4.5 mm. Other plates can also be used in a similar way.

With either arrangement, or in the case of many more pins, the method is performed under computer control to form a more densely packed array of fluid dots than that occurring in the multiwell plates, e.g. arrays of 20 micron to 375 micron diameter dots with similar spacing between dots, using all fluids in the plate.

Just as the pins are located on 9 mm centers, the square arrays themselves are distributed on 9 mm centers over the face of the substrate. By following an appropriate pickup sequence by repeated samplings, all wells are visited, the pins being conveyed under computer control to the cleaning station between changes of fluids. The contents of the multiwell plate or a number of plates are thus distributed from the low density distribution of wells in multiwell plates to high density arrays.

Similarly, again using 9 mm pin spacing, with two rows of 6 pins each, a sequence of samplings from the wells under computer control collects samples from all wells and uniquely distributes them as high density array deposits in 12 squares on the microscope slides or other substrate.

The benefit of such groups of pins is to create a large number of deposited dots simultaneously on one or many microscope slides or substrates. This can substantially reduce the time and cost required to create high density arrays.

The assemblage of pins on a 9 mm square grid can also be used to transport fluid from plates with well spacing constructed on a square grid that is based on sub multiples of 9 mm, such as plates with 384 wells or 864 wells or 1536 wells, etc. The high accuracy of the computer controlled gantry system enables accurate placement of the selected wells with respect to the pins, and the pins with respect to the receiving substrate and the cleaning station.

It is evident that using the same logic, pins can be assembled in denser constructions to fit plates with smaller well spacings.

The denser the array, the tighter the location tolerances for the location of each small dot. The systems of laterally constrained deposit pins described in the PCT Application PCT/US99/00730 (which is hereby incorporated by reference) are particularly capable of repetitive production of precise high density arrays. In the embodiment of 4A, the mounting tube, at its lower end, is shown to have been spun, to form a generally conical bottom ledge that, in interacting with a downwardly facing conical surface of the pin, tends to center the pin. Using these principles, the mode of supplying the tips with fluid can be selected in reference to the nature of the fluid as well as other operating parameters. A ring supply mode will now be described.

PIN & RING SYSTEM

Figure 4:
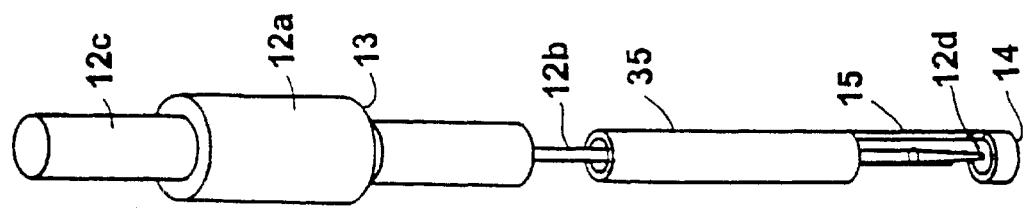
FIG. 4 is a perspective view of an assembled deposit pin constructed according to FIG. 4A combined with a respective supply ring.
Figure 5:
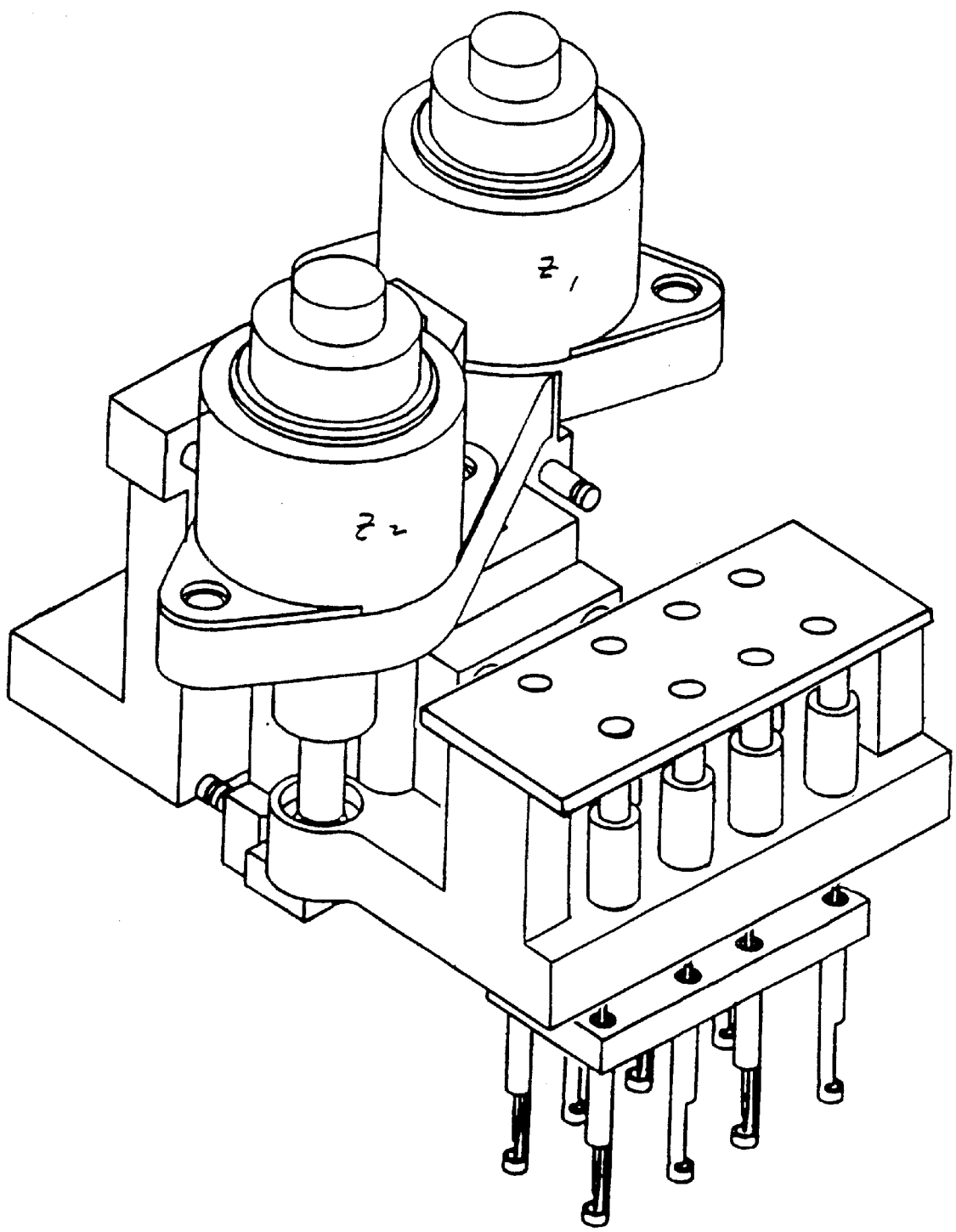
FIG. 5 illustrates an arrayer system, employing a group of assemblies of FIG. 4 constructed for commercial use.

The pin assemblies as shown in FIG. 4A and in Figures of the cited PCT application can be used with a simple axial ring translation mechanism. As the fluid needs 10 to be picked up from a rather large well, a sufficiently compact arrangement of multiple pins and supply rings is possible. FIG. 4 shows the relationship of a pin and ring without their support or actuation mechanisms. Seen in FIG. 4 are supply ring 14, pin tip 12*d*, ring body 35 from which a support rod segment 15 extends to the ring 14, pin shaft 12*b*, the pin seat 13 formed on pin body 12*a* and pin guide 12*g*. FIG. 5 shows a set of eight such pin and ring assemblies. It is evident that any number can be assembled in this fashion. In FIG. 5 one can see the pin holding structure, and the ring holding structure and their respective linear stepper motors $Z_1$, and $Z_2$ that enable relative vertical motion. The $Z_1$ motion for deposit on a receiving surface preferably involves overtravel, the compliance of the deposit pins relative to the receiving surface, as provided by spring 22 in FIG. 4A, ensuring proper deposition over a range of surface heights. The respective supporting linear guide rails for X and Y motion provide a complete array-forming mechanism. FIG. 5 illustrates a commercial realization of the design which attaches to the Y stage linear motor of a deposit system.

Deposit pin 12 can also be mounted on a parallelogram, cantilever construction or as described in the PCT application incorporated by reference.

FIG. 2 suggests a deposit cluster 28 of independently operated deposit pins, formed by a number of the deposit assemblies described in the FIGS. 2A, 2, 4 and 4A. These employ a number of independent drives D, one to drive each pin and one to drive each ring in Z direction for picking up and depositing fluid, and sensors to indicate to the control electronics the position of the operative elements.

The cluster may step to a selected X or selected X,Y position, at which a number of different motions under computer control may be caused to occur, picking up and depositing fluid in any order at any location desired, and visiting the cleaning station as required. Such a cluster constitutes a particularly versatile tool when employed with conventional microtitre plates.

In such embodiments the aliquot carrier rings 14 and pins 12 are spaced in the cluster at 9 mm center-to-center distances or multiples thereof to facilitate operation with 96 well plates (in which the wells are spaced at 9 mm on center intervals, with 8 rows of 12 holes). Higher density plates also employ this configuration and have the same footprint but employ more holes, 16×24, with hole-to-hole resistance of 9/2 mm, to provide "384 plates". The system described can be employed with 96 and 384 well plates, as well as any arbitrary arrangement.

The versatility of the cluster of independently operable deposit pins is illustrated by the following examples.

An array of sub-reservoir rings, e.g. set at 9 mm center-to-spacing, may be indexed in X,Y direction along with their pins and the rings may be driven down (or dropped) simultaneously into respective cleaning cavities or for supply or resupply from four wells of a conventional 96 or 384 well plate, in an action similar to the systems previously described.

After suitable indexing, the set of pins may be driven down simultaneously to form deposits at a corresponding number of places, in the same format as the supply plate.

Alternatively, during resupply, one sub-reservoir ring may be dropped to pick up material from a selected well while all others remain in their passive positions. Then the cluster may be moved until the next ring arrives at the same well or another selected well, at which point it is dropped to pick up its aliquot, and so on, so that all of the rings may have the same fluid from the same wells or different fluid from any selected wells.

The cluster 28 may be moved in X,Y direction between pickup or deposit actions of successive pins so that, e.g. all of the pins deposit the same or different fluid on a single slide at selectable addresses or each pin addresses a different slide, but at a different location, or two pins address one slide and two another slide, or the deposits are made one on top of another, etc.

The operator may also choose not to have one or more of the devices operating.

Thus it is seen that dense clustering of independently operable deposit pins and rings can enable high speed, versatile operation.

Actuation of all aliquot carriers simultaneously by one actuator and all pins actuated by another single actuator, to provide a multiple pin head, realized with flexure-mounted pins is also possible. For example, using linear stage techniques, two rows of four pins at 9 mm spacing in both X and Y directions are all mounted on a frame which is reciprocated along a rail via a carriage by a single motor. This causes the eight pins to move simultaneously. Likewise, two rows of four cooperating rings 14 are mounted on a common ring support 124, with the same spacing. The single support is driven via carriage by one motor.

Figure 8:
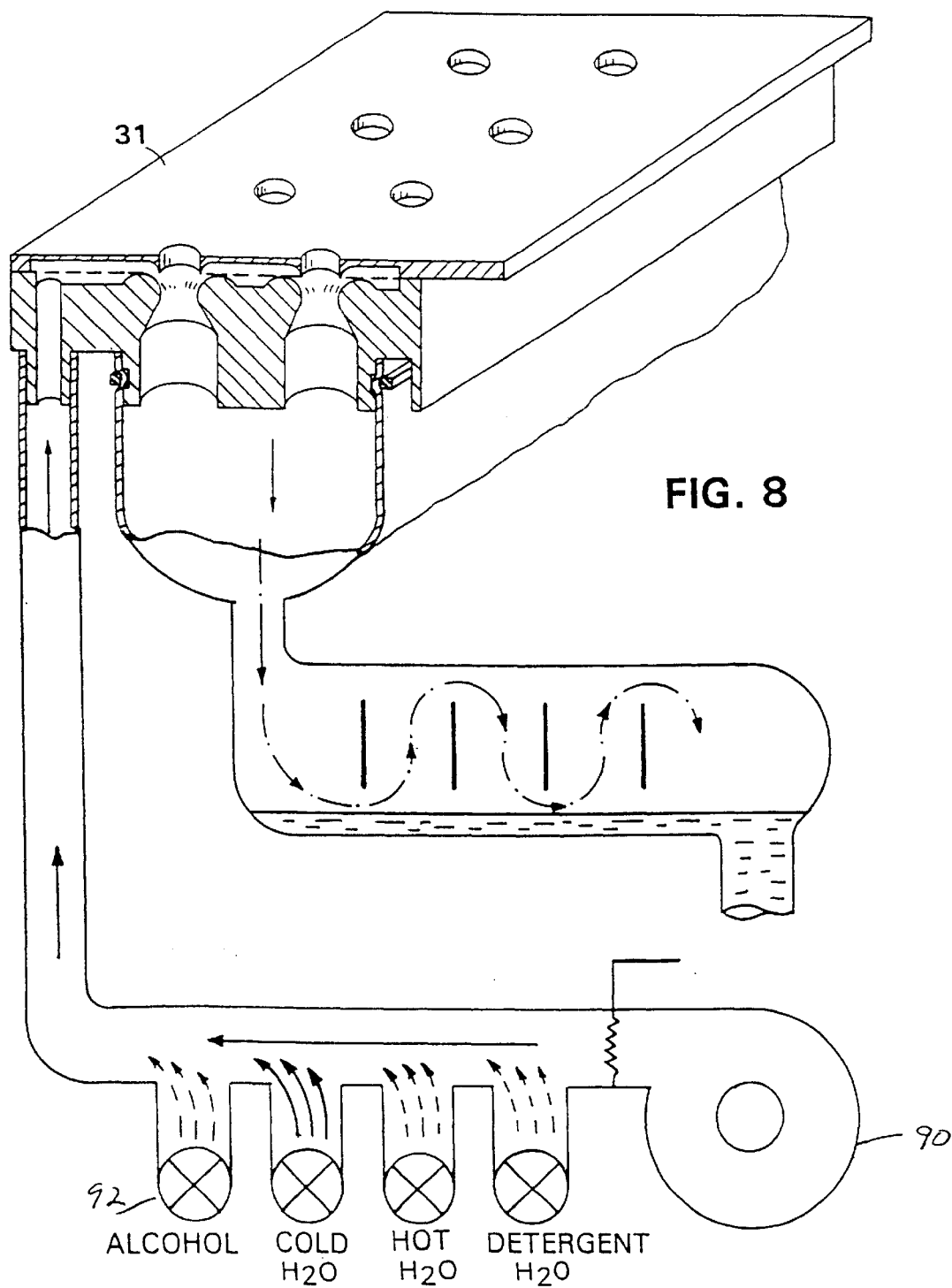
Figure 9:
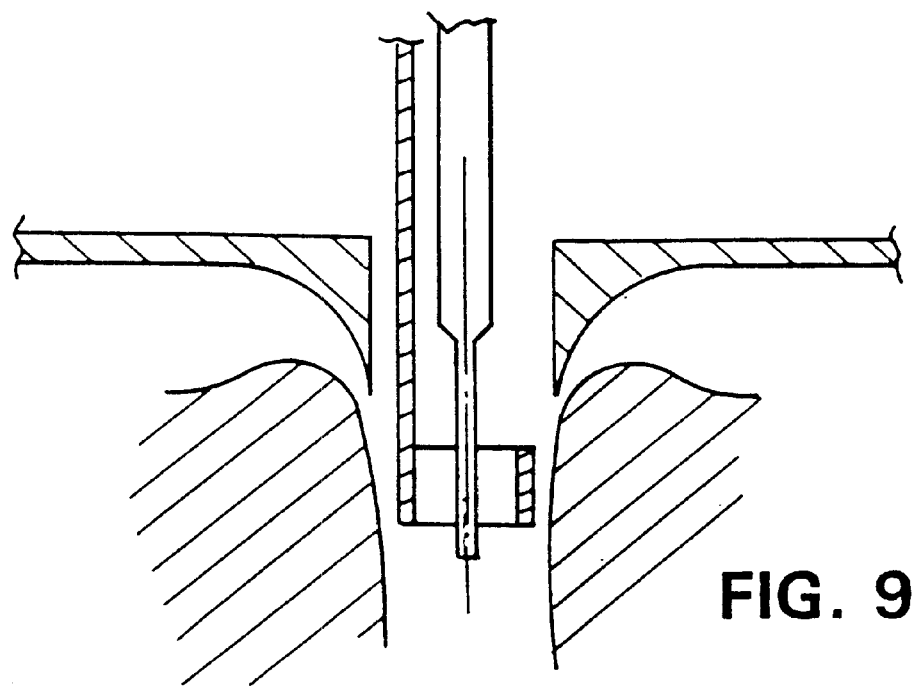
Figure 9A:
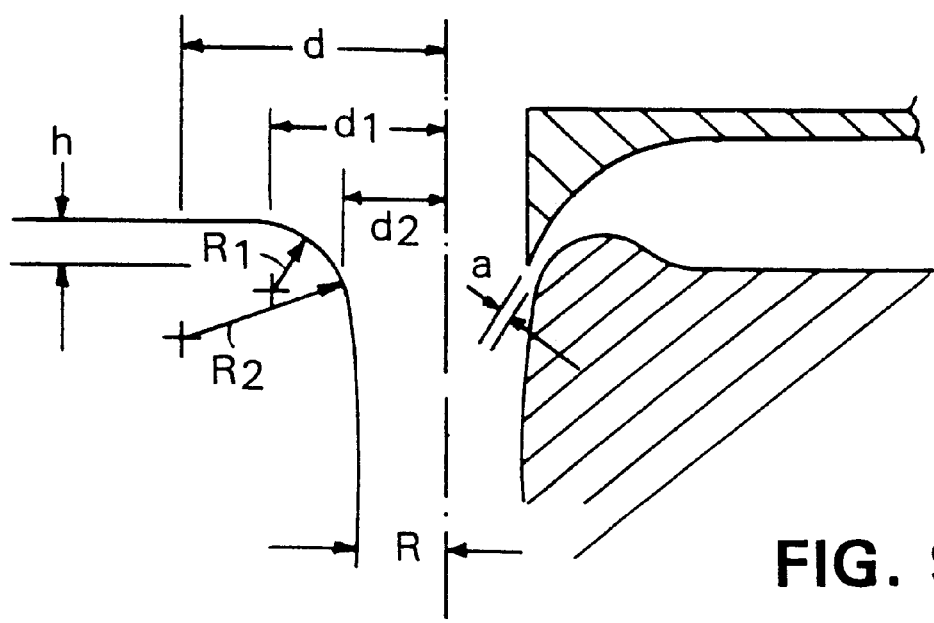
FIG. 9A illustrates certain dimensions other embodiments of FIG. 9.
Figure 10A:
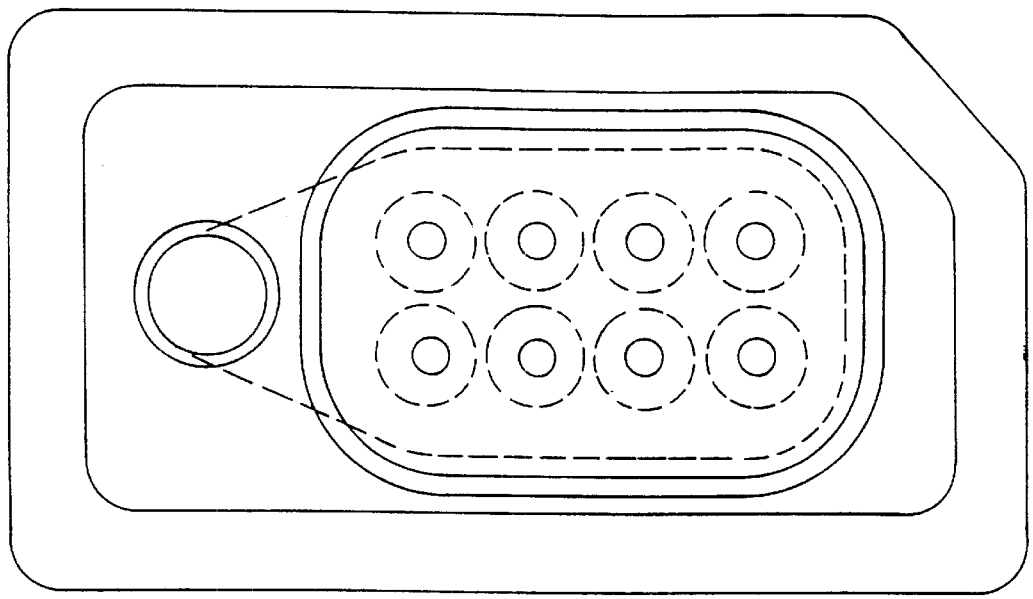
FIGS. 10 and 10A are side and bottom constructional views of the module of FIGS. 8 and 8A.
Figure 10:
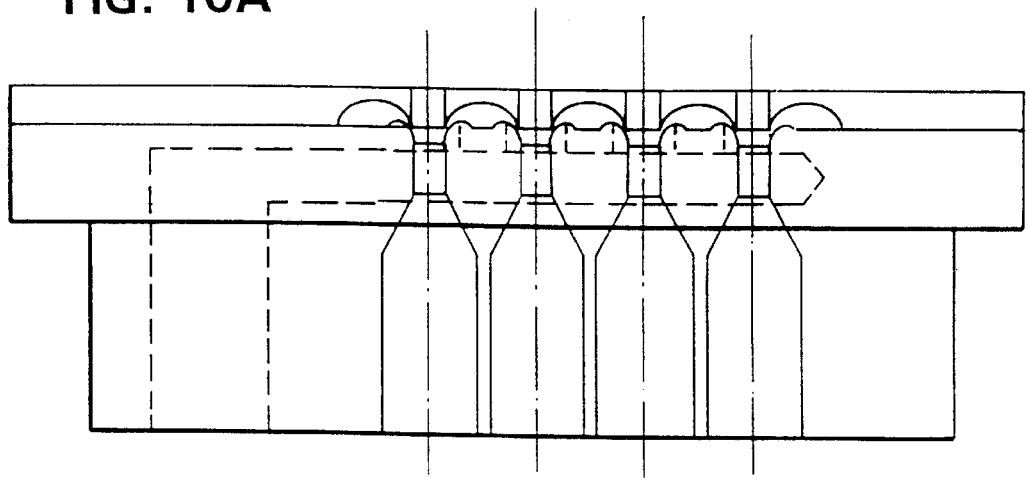

Referring to cleaning stations CL in FIGS. 1, 2 and 6, 6A and 7 and the detailed views, FIGS. 8–10, a preferred cleaning and drying station for a set of pin and ring assemblies for plain pins or other tools used in the environment, employs a corresponding set of venturi passages in which respective pin and ring assemblies, pins or tools are introduced. This provides "one-stop" shopping for a set of cleaning conditions such as alcohol denaturing, cold water rinse, detergent wash, hot water rinse, hot air dry. A supply plenum is fed with pressurized fluid of selected quality from an air compressor 90, nitrogen tank, etc. In one example compressed air is employed for all cases, into which are selectively introduced by controls suggested by valves 92, agents to create the respective aerosols of water, soapy or detergent solution, alcohol, etc., followed by heated air for drying, as produced by the resistance heater in the air flow path.

CLEANING

High density microarrays require spotting tools with correspondingly small features. The smaller the features, the more difficult it is to clean and prevent contamination.

The downwardly directed set of venturi passages of FIGS. 8 and 8A, to which the tools gain access by entering from the top of the chamber, is a very effective means of cleaning in many ways. First, it produces high pressure cleaning; second it enables the selection of the temperature of the fluid or air without moving the pins or rings; and it can be very efficient. In certain cases, the high velocity air may drag or accelerate washing fluid or may entrain abrasive elements, for instance beads of polyethylene or other material with the simple use of fluid under pressure to provide the energy for the cleaning.

Figure 6:
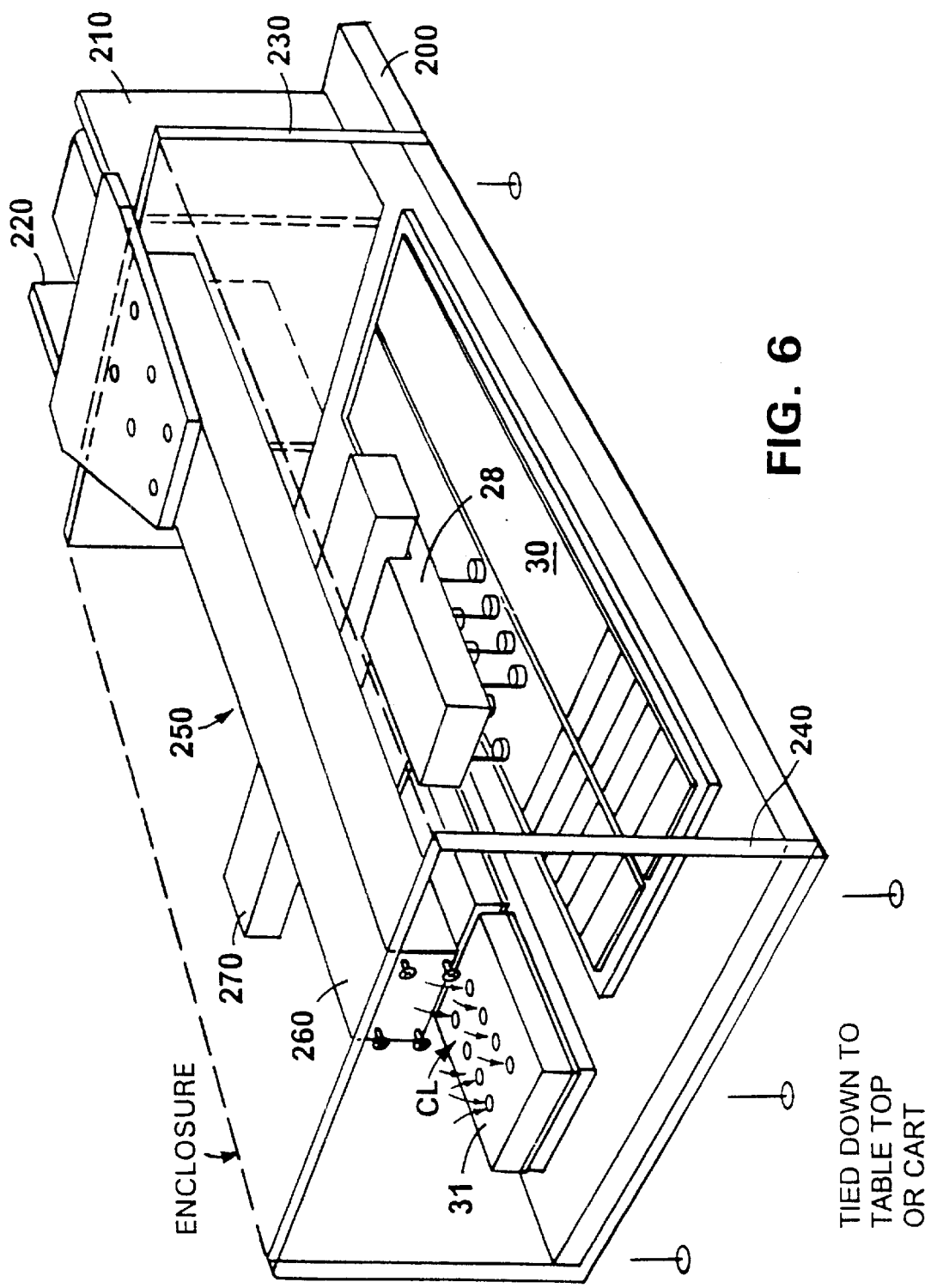
FIG. 6 is a perspective view of a machine for depositing dots of biological fluid in dense array upon a series of microscope slides.
Figure 6A:
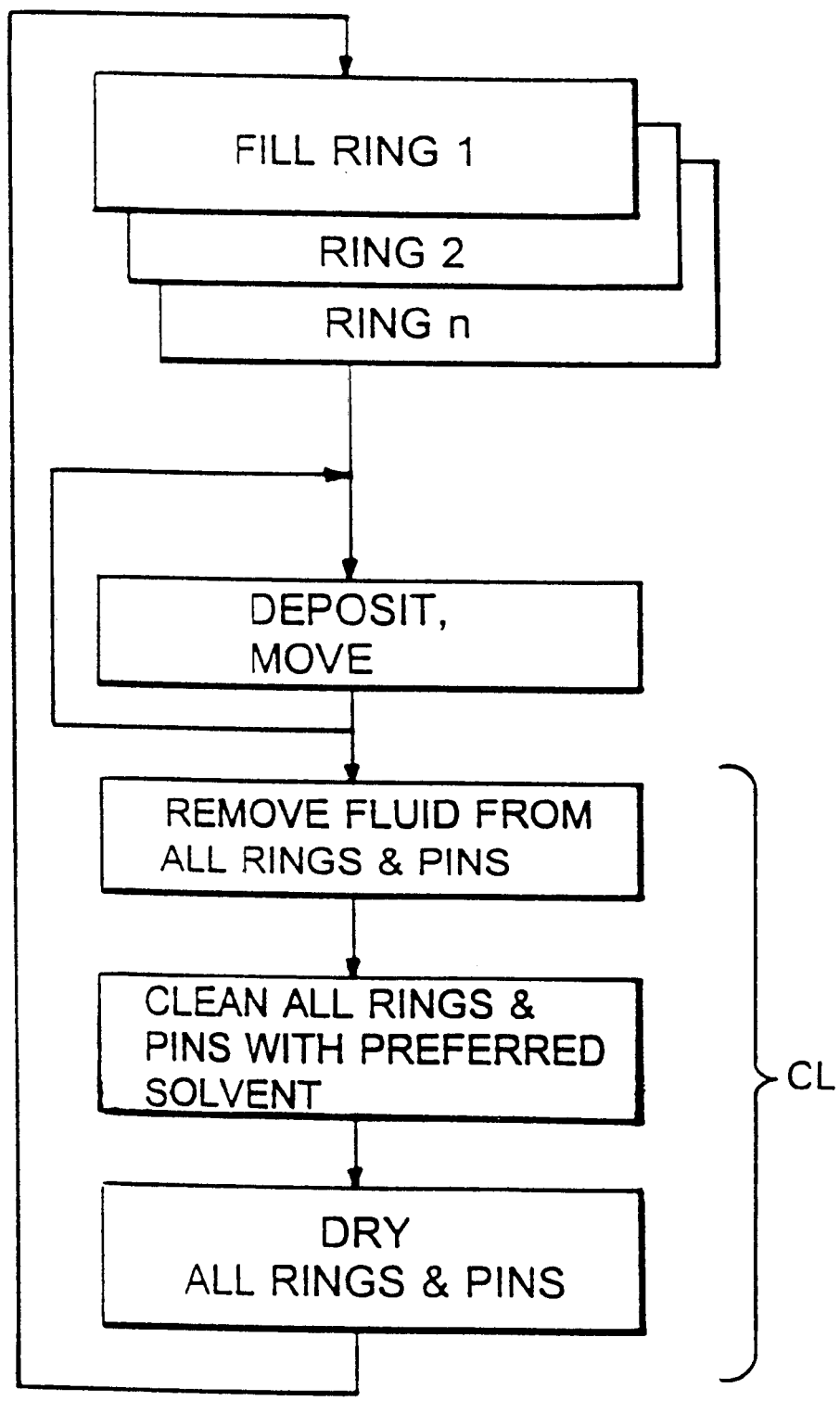
FIG. 6A shows features of the control system software and method for conducting the deposit and cleaning action.

From the point of view of infectious or dangerous material, the benefit from this new mode of cleaning is that the contaminant will not escape into the working zone, such as the enclosed spotting area of the arrayer in FIG. 6. The enclosure ensures that the instrument is situated in a controlled environment. The flows of the venturi tubes are arranged to have an evacuator or pump effect, drawing (i.e. entraining) air from the working zone and preventing contaminating back flow from the cleaning chamber.

This type of cleaning is especially useful for the arrayer, but more generally has broader potential as a cleaning station for small instruments, in particular where escape of contaminants is to be avoided, for instance in a hospital or food preparation setting. The jet is aimed down from the access portals at the to of the module, through which the devices to be cleaned enter. Because of the contained nature of the jet action one may employ very high fluid pressure, high temperature and strong cleaning agents while the immediate environment is protected from contamination or disturbance. Thus adaptations of the principle provide a nearly universal cleaning tool for biological and other laboratories. The air jets enable reaching surfaces to which access is difficult. The fluid agent or the cleaning agents are contained in all directions and do not escape. They do their work of cleaning while being contained and are retrieved and disposed of with little chance of escape.

The system comprises basically a containment chamber with entry portals sized for introducing of a work object, especially a pin and ring deposit assembly. The oriented jets directed away from the access portal, convey fluid against the devices to be cleaned that can dissolve coatings or contamination. The entry manifold enables injection of fluids for dissolving, washing and drying that can be sequenced without moving the parts being cleaned. The system easily interfaces with a logic system or computer to achieve automated cleaning action. The system is particularly well suited for microbiology and gene research deposit assemblies that are arranged in high density to produce microarrays.

ARRAYER

The gantry of an arrayer, now to be described, can carry one deposit head, a cluster of independently operable single pin heads, or a multiple pin head of the various designs described above. Combinations of these are also possible.

FIG. 6 is a perspective view of a slide preparation machine for preparing microscope slides or other substrates such as delicate soft or porous membranes carried on rigid supports. Its function is to rapidly deposit a high density array of fluid dots of different compositions on a number of identical substrates, employing the microdot technology. As shown in FIG. 6, there are a number of 96 well supply plates 31, serving as the central fluid source for resupply of mobile fluid storage devices, and a cleaning station CL.

Horizontal base plate 200 provides a support structure to hold the operating components. Fastened to base plate 200 are vertical sub plates 210, 220, 230 and 240. Fastened to these plates is a dual axis motion system 250, comprising X and Y axis devices 260, 270 for providing X and Y motions, in a parallel plane.

The guide rails of the X and Y axis devices, 260, 270 are parallel to base plate 200, to carry deposit cluster 28 in X,Y motions in a plane parallel to base plate 200.

The X axis device 260 is a commercial device available from Adept of Japan. It moves at a high rate of speed in a controlled manner using a rotary servo motor with a drive screw and a shaft position encoder, employing digital and analog technology. Carried by X-axis device 260 is an orthogonally arrayed Y-axis device 270, which is a smaller version that operates in the same manner as the X-axis device.

The deposit cluster 28 comprises eight deposition mechanisms, ganged together on a mounting structure. These devices may be in accordance with the various structures shown.

After a deposition sequence is complete, the X and Y terminal drives the cluster of depositing elements to the cleaning station CL. In some embodiments they may be passed over the wells from which the fluid originated or other receptacle and subjected to air blast as by the venturi passage of the cleaning block described, to dislodge excess fluid, or excess fluid may be removed by abrupt stopping of rapid downward movement to dislodge excess fluid.

The fluid removal station according to FIG. 7 is a schematic version of the arrangement of FIG. 8, where air flow removes remaining fluid from the pins and rings. The array of pins and rings is purged of remaining fluid by air blast and then by warmed air (or other gas). The array of pins and rings is washed and rinsed by liquid or aerosol streams and dried, while remaining stationary.

As an alternative to the top access multiple venturi scrub chamber in the system of FIG. 6, the array of pins and rings of a cluster 28 may be held over a vessel of water for cleaning, in which the water level is maintained and a pump constantly replenishes the water. Blotting paper or a cellulose sponge may be provided against which the pin and ring are blotted for fluid removal or drying. By considering the relative clumsiness of such techniques, one gains a better understanding of the significance of the venturi chambers described.

The control system of the arrayer of FIG. 6 has controls for the X and Y axis movement and also home center for the X and Y axis. The actual position of the carriage that the lead screw is driving is sensed so the carriage can be driven home and then the counter is initialized so precision motions can be made along both the X and Y axes. As previously described, each deposition head may have two motors, a pin drive motor and a ring motor, which are commanded from the control computer.

For deposit on microscope slides including slide-like rigid members carrying delicate, soft membranes, the slides are fastened to the table, or placed in register with guides in a known position. Features on the base plate of the machine locate the slides in predetermined orientation.

For use in high volume production contexts, the system described in the foregoing figures preferably employs a rapidly moving, laterally constrained, axially compliant pin as shown in FIGS. 4 and 4A, in a deposit cycle of less than 0.1 second, in which impact and vibration is minimized, with the natural frequency of the system more than 10 Hz, in many cases preferably 20 Hz, a pin contact pressure of less than 1.0 gram, preferably less than 0.5 gram in many cases preferably about 0.3 gram, and the system employing damping.

Each pin as shown in FIG. 4A is mounted in its own mounting tube by threading into a header plate, and can be readily individually removed and replaced for service or for providing pins or different sizes appropriate to different protocols.

Pin pressure on the substrate is light, and fluid splatter or separation conditions are thus avoided, despite the high speed of action, so that dots of fluid of uniform shape are consistently formed at precisely controlled positions, even on soft or fragile receiving surfaces, thus providing more accurate arrays, and as well, keeping the nearby environment clean and free of tapping or impacting elements.

In the deposit action of the deposit pin, by raising the pin after contact of the drop on the substrate, the combined effects of inertia of the stationary fluid and surface tension (and of gravity, when depositing downwardly, which is normally preferred) act upon the drop of fluid to overcome the force of surface tension exerted by the lifting pin. The fluid drop preferentially stays with the surface of the substrate, and the pin, substantially devoid of fluid, is free to be replenished and move rapidly to its next destination.

As the volume of the fluid is accurately specified by use of standard sizes of pin, and standard conditions, and the position of the pin is precisely constrained as by the mounting tube of FIG. 4A, spots, dots and microdots of consistent size and precise location are produced, that enable an improved degree of quantification of observed results. In particular, this is of importance in support of the new field of quantified fluorescence microscopy.

D. EXAMPLES OF NOVEL METHODS OF USE

The systems described are useful with any native fragment of DNA, or pre-synthesized oligonucleotide of any length. There being no restriction as to chemicals, any non-photoreactive chemical as well as photoreactive chemicals can be employed. Likewise dyes that are useful to detect presence or absence of DNA may be selectively deposited in registry with previously deposited spots or microdots of biological material, and vice versa. Indeed, in one example, the accuracy of the spotting technique employed here, is capable of spotting standard fluorescing sample dots that can be employed as a calibration standard for the instrument to support quantified fluorescence microscopy.

Among the many biological materials that may be spotted at high speed are fragments of nucleic acids, e.g. DNA, RNA or hybrids such as PNA (peptide nucleic acid), PCR (polymerase chain reaction) products, cloned DNA, and isolated genomic RNA or DNA, as well as synthetic analogs.

Also included are restriction enzyme fragments, full or partial length cDNA, mRNA or similar variations thereof, proteins such as protein receptors, enzymes, antibodies, peptides and protein digests; carbohydrates; pharmaceuticals; microbes including bacteria, virus, yeast, fungi, and PPLO; cells and tissue fragments; lipids, lipoproteins, and the like; plastic resin polymers, small particulate solids in suspension, etc.

The deposition system may also be employed to deposit catalysts, reagents and encapsulants upon previously deposited material of any of the types above or, as mentioned below, to create an array of sites or micro-wells for later reaction or growth of such material, or to assist in neutralizing or cleaning the deposit or reaction sites, as in the case of highly toxic or virulent substances. The high effectiveness and containment provided by the cleaning system enables working with virulent or dangerous materials that can enable safer diagnostics and disease control, and can extend the range of useful reactions that may be investigated.

The most basic use of the arrayer is to create high density arrays of nucleic acid on a porous or solid, flat surface, generally a microscope slide or slide-like support. Deposit is possible on fragile or soft surfaces such as microporous membranes or gels, glass cover slips, plastic surfaces, and wells of a microplate, or any substrate, which may be previously coated or derivatized, and serve as a recipient surface.

In particular, membranes and gels are desirable to enable high density analysis with automatic equipment, using materials familiar to the field, on which much of the important, historical data has previously been acquired. Also, deposit on fragile glass cover slips is desirable as they are thinner than microscope slides, easier to maneuver, and when a beam of light is transmitted through them for transmission microscopy, better light capture occurs because the slip is thinner and less light absorptive. The system has the capability of spotting on plastic surfaces without scarring or deforming the surface.

In addition to applicability in bioresearch and clinical diagnosis, the deposition and instrument cleaning system has applicability in the chemical laboratory, e.g. to analyze fluids, such as for water quality, or to experiment with resins, for instance polymerization reactions, to conduct experiments in small quantities of many different varieties, e.g. to determine optimum ratios and optimum selection from a host of slightly varying examples. The range of usefulness is broad with application to the new, popular paradigm of a large number or simultaneous experiments based on small quantity samples, different temporal sequences, different kinetics of reaction, and different mixtures. In all of these cases, the deposit and cleaning system is a precise way of manipulating small amounts of liquid, solids in liquid suspension and cells in suspension, under controlled and safe conditions.

Deposition with the systems described leads to rapid and precise observations, reduction in the number of trials for a given experiment and improvement in the statistical significance of the data. Cost savings and improved experimental procedures can be realized. Quantification of results at accuracies heretofore unknown may be attained by consistent and precise dot formation that enables improved signal-to-noise ratio in detection, when sensing the difference between, e.g., the fluorescence of a deposited spot and the immediately adjacent background surface of the substrate.

The system is useful in many environments due to the attributes of the deposit and cleaning apparatus, and the techniques by which movement and control is effected.

In another method employing the deposit and cleaning system, an etchant fluid is provided in a local reservoir ring. The pin of the deposit pin distributes the etchant in tiny, precise spots or microdots in a desired array across a reactive substrate surface. For instance, for forming micro-wells for containing fluid, the device deposits an acid such as hydrochloric acid in an array of small dots upon a silicon substrate. An etching reaction occurs, and the substrate is then neutralized and washed, to produce a corresponding array of small wells, after which the tools of the arrayer may be washed of etchant without risk of contamination or harm to the adjacent activities.

Arrayers as described can also be used for color printing of fabrics, paper etc., where the 96 well plate holds different color inks or dyes. The area to be printed is the entire reach of the gantry less the color source and washing station.

The arrayer can be used to generate a single printed circuit board, e.g., prototype boards, or boards for limited volume production, where the machine is employed to deposit varnish or photoresist or other protective coating material to define the regions of the copper clad or other substance which need to be preserved from acid etching. Likewise the arrayer may be employed to deposit photoactive substance for production of "biological" deposits using lithographic techniques, all with the assurance that the deposit elements will be cleaned to avoid cross-contamination.

A variation of the spotter mechanism employs, in a fashion analogous to that of a modern milling machine, a set of interchangeable heads having different capabilities. Under computer control, an X-Y carriage of the system is moved to select a desired head that is carried across the substrate to be cleaned and perform its function. In some instances the device selected may be a sub-reservoir ring from a set of such rings that have different internal diameters or are formed of different wire or ribbon sizes, or are of different sizes to enter different wells, etc. These provide a variety of carrying capacities for fluids of different viscosities or for use with deposit pins of different sizes. Likewise, different sizes of deposit pins can be selected from a set of pins to vary the size of the spot to be deposited. Heads can also be selected that provide other devices for preparing for or conducting experiments or for the production of reference or diagnostic well plates and slides.

In some cases the selection and use of devices can be conducted under complete computer control to enable automatic performance of a multi-task experiment un-attended by the technician, in which the tools or devices are subjected to automated cleaning, e.g., with the system of FIG. 8, during the regular course to avoid contaminated experiments.

In addition to depositing spots of fluid upon a standard microscope slide, and upon porous or soft membranes and other delicate substrates, it is possible and advantageous to deposit spots on substrates of significantly larger area and on other substances and on surfaces having special formations, for instance upon substrates having micro-cavities that have been formed by the instrument itself, by one of the techniques described above. Plates delivered with the micro-cavities preformed in the substrate may also be used, and aligned for deposit of fluid by automatic controls of the instrument, or the control system of the unit is advantageously provided with a vision system that "reads" the location and pattern of the array of micro-wells, and adjusts itself automatically or under operator control to accurately deposit dots of fluid in wells. Likewise a vision system can be employed to identify different types of cleaning chambers that have been installed, e.g. by bar code identification to ensure that each device to be cleaned enters a suitable chamber into which it fits and which has appropriate features for cleaning imaging special features of the tool or other device.

F. CONCLUSION

In the various ways described, a large array of fluid deposit sites may be established and managed in a precise, repeatable manner that employs the same concentrations or reactions or precisely varied concentrations and reactions, under conditions that prevent contamination and enable high speed or automatic action. This may be done to enable examination, to promote reaction or growth processes in biotechnology, life sciences, chemistry, pollution detection, process control and in Thus, beyond an instrument for low-cost preparation of microscope slides and membranes for biotechnology research, there has been contributed a universal and widely variable set of systems, instruments, methods and products that can advance research and industry.

Numerous other embodiments not described in detail here can apply the principles described to particular applications and are within the scope of the claims.

What is claimed is:

1. An apparatus for depositing an array of spots on a receiving surface, comprising:
   a deposit device, including a drop-carrying surface, and a fluid source cooperatively arranged to deposit a spot on a receiving surface; and
   a cleaning device constructed and arranged to clean said drop-carrying surface by employing a flow of cleaning fluid arranged to prevent contaminating back flow.

2. The apparatus of claim 1 wherein said cleaning device includes a venturi fluid jet constructed and arranged to blow said cleaning fluid.

3. The apparatus of claim 2 wherein said fluid jet is also constructed to deliver drying fluid.

4. The apparatus of claim 3 wherein said fluid jet includes a circular nozzle constructed to emit a conical flow of said cleaning and drying fluid.

5. The apparatus of claim 3 wherein said fluid jet includes a circular nozzle constructed to sequentially emit a conical flow of said cleaning and drying fluid.

6. The apparatus of claims 4 or 5 further including a reservoir for receiving said cleaning and drying fluid.

7. The apparatus of claim 6 further including a vacuum pump associated with said reservoir.

8. The apparatus of claim 3 including at least two fluid paths associated with at least two fluid reservoirs and connectable to said fluid jet.

9. The apparatus of claim 1 wherein said cleaning device includes a venturi fluid jet constructed and arranged to blow said cleaning fluid at least partially along a length of said deposit device toward said drop-carrying surface.

10. The apparatus of claim 9 wherein said drop-carrying surface is located at least partially within a confinement chamber and said flow of cleaning fluid is arranged to prevent contaminating back flow from said confinement chamber.

11. The apparatus of claim 10 wherein said drop-carrying surface has a diameter less than 375 micron.

12. The apparatus of claim 11, wherein said drop-carrying surface has a diameter less than 300 micron.

13. The apparatus of claim 12, wherein said drop-carrying surface has a diameter between about 15 and 250 micron.

14. The apparatus of claim 2 or 9 wherein said fluid jet includes a circular nozzle constructed to emit a conical flow of said cleaning fluid.

15. The apparatus of claim 2 or 9 wherein said fluid jet includes an annular nozzle constructed to emit a flow of said cleaning fluid.

16. The apparatus of claim 2 or 9 further including a reservoir for receiving said cleaning fluid emitted from said fluid jet.

17. The apparatus of claim 16 further including a vacuum pump associated with said reservoir.

18. The apparatus of claim 1 wherein said deposit device has a pin-like structure with said drop-carrying surface disposed in a distal end of said pin-like structure and there is associated a ring-like structure encircling said pin-like structure.

19. The apparatus of claim 18 wherein said pin-like structure includes sides that intersect with an end surface that defines a rim of said drop-carrying surface.

20. The apparatus of claim 1 further including a mobile supply device, associated with said deposit device, and arranged to supply material for deposition of said array of spots.

21. The apparatus of claim 20 wherein said deposit device has a pin-like structure including said drop-carrying surface and said mobile supply device includes a mobile local supply device arranged to move partially with said pin-like structure.

22. The apparatus of claim 21 wherein said cleaning device is constructed and arranged to deliver said cleaning fluid at least partially to said mobile local supply device.

23. The apparatus of claim 21 wherein said mobile local supply device includes a ring-like structure located near said drop-carrying surface.

24. The apparatus of claim 23 wherein said cleaning device is constructed and arranged to deliver said cleaning fluid at least partially to said ring-like structure and said drop-carrying surface.

25. The apparatus of claim 21 wherein said mobile local supply device includes an annular member through which said deposit device operates by a relative motion of said drop-carrying surface, and said cleaning device includes a nozzle for directing a flow of said cleaning fluid past said annular member and said drop-carrying surface.

26. The apparatus of claim 20 wherein said deposit device and said mobile supply device are movable together to said cleaning device in response to a control system.

27. The apparatus of claim 20 further including a drying device constructed to discharge drying fluid.

28. The apparatus of claim 20 wherein said mobile supply device is movable relative to an array of deposit locations, said mobile supply device being constructed and arranged to store deposit fluid and resupply the deposit device at various locations along said array.

29. The apparatus of claim 28, wherein the deposit device and the mobile storage device are constructed to supply drops to the deposit device in the immediate vicinity of the deposit locations for respective drops.

30. The apparatus of claim 28 or 29, wherein the deposit device and mobile storage device are coupled for movement of the deposit device toward and away from the receiving surface.

31. The apparatus of claim 1 including a control system arranged to control a flow velocity of said cleaning fluid.

32. The apparatus of claim 1 including a control system arranged to select a type of said cleaning fluid.

33. The apparatus of claim 32 wherein said control system is arranged to select said type of said cleaning fluid at a source location.

34. The apparatus of claim 1 wherein said cleaning fluid is selected from one of the following compressed gas, high pressure liquid, aerosol and heated gas.

35. The apparatus of claim 1 including at least four said deposit devices and including a mechanism for moving each said deposit device independently toward and away from the receiving surface to deposit respective drops at respective deposit locations on the receiving surface.

36. The apparatus of claim 1 including at least four said deposit devices and including a mechanism for moving said deposit devices simultaneously, relatively, toward and away from the receiving surface to deposit respective drops at respective deposit locations on the receiving surface.

37. The apparatus of claim 36 wherein said deposit devices are mounted on a common support that is driven by a common driver to deposit respective fluid drops on the receiving surface.

38. The apparatus of claim 36 wherein each said deposit device is associated with a respective storage ring, the storage rings being mounted on a common storage support driven by a common storage drive.

39. A method of depositing a biological material on a substrate, including:

mechanically lowering a pin-like structure including a drop-carrying surface to a substrate and thereby depositing by contact a drop of biological material;

moving said pin-like structure to a cleaning station; and emitting a flow of cleaning fluid toward said drop-carrying surface, said flow being arranged to prevent contaminating back flow.

40. The method of claim 39 including collecting at least a portion of said emitted cleaning fluid in a confinement chamber, wherein said flow of cleaning fluid is arranged to prevent said contaminating back flow from said confinement chamber.

41. The method of claim 40 including pumping fluid from said confinement chamber.

42. The method of claim 39 wherein said emitting includes directing said cleaning fluid along said pin-like structure toward said drop-carrying surface being surrounded by a ring-like structure forming a mobile local supply device.

43. The method of claim 39 including emitting a drying fluid after emitting said cleaning fluid.

44. The method of claim 39 providing at least two fluid reservoirs, and the method including, after said emitting, switching to a second-mentioned reservoir and emitting fluid from said second-mentioned reservoir.

45. The method of claim 39 further providing multiple flow nozzles and at least one confinement chamber, the method including emitting multiple flows of said cleaning fluid through said flow nozzles located at said confinement chamber.

46. The method of claim 39 including emitting at least one of the following: compressed gas, high pressure liquid, aerosol, and heated gas.

47. A method of depositing a biological material on a substrate, comprising:

receiving on a drop-carrying surface of a pin-like structure a first type of a biological material drop;

mechanically lowering said pin-like structure toward a substrate and thereby depositing by contact from said drop-carrying surface said biological material drop of said first type;

moving said pin-like structure to a cleaning station including a confinement area;

emitting a flow of cleaning fluid toward said drop-carrying surface, said flow of cleaning fluid being arranged to prevent contaminating back flow from said confinement area;

receiving on said drop-carrying surface a second type of said biological material drop; and mechanically lowering said pin-like structure toward said substrate and thereby depositing by contact from said drop-carrying surface said biological material drop of said second type.

48. The method of claim 47 wherein said depositing of said biological material drop of said second type is performed on a location of said substrate that is overlapping with a deposited location of said first type drop on said substrate.

49. The method of claim 47 wherein said depositing of said biological material drop of said second type is performed on a location of said substrate that is different from a deposited location of said first type drop on said substrate.

50. The method of claim 47 wherein both said receiving acts are performed by using a mobile supply device.

51. The method of claim 50 wherein said mobile supply device includes a 96 well plate.

52. A The method of claim 47 herein both said receiving acts are performed by using a local mobile supply device.

53. The method of claim 52 wherein said local mobile supply device includes a ring-like structure located near said drop-carrying surface.

54. The method of claim 53 wherein said emitting of said flow of cleaning fluid includes directing said flow partially along said pin-like structure past said supporting surface and partially through said ring-like structure.

55. The method of claim 54 wherein said receiving on said drop-carrying surface said second type of said biological material drop includes dipping said ring-like structure into a well of a well plate.

56. The method of claim 39 or 47 wherein said biological material includes fluorescing material, an ink, dye, stain or marker, a photoactive material, radioactive material, a varnish or encapsulant, or an etchant.

* * * * *